(12) United States Patent
Bradu

(10) Patent No.: US 9,579,057 B2
(45) Date of Patent: Feb. 28, 2017

(54) SYSTEM FOR MULTIDIMENSIONAL ANALYSIS, MODULATION AND OPTIMIZATION OF FACIAL EXPRESSIONS

(71) Applicant: Stefan Bradu, Rego Park, NY (US)

(72) Inventor: Stefan Bradu, Rego Park, NY (US)

(*) Notice: Subject to any disclaimer, the term of this patent is extended or adjusted under 35 U.S.C. 154(b) by 196 days.

(21) Appl. No.: 14/100,885

(22) Filed: Dec. 9, 2013

(65) Prior Publication Data

US 2015/0157259 A1 Jun. 11, 2015

(51) Int. Cl.
*A01B 5/00* (2006.01)
*A01B 5/16* (2006.01)
*A61B 5/00* (2006.01)
*A61B 5/16* (2006.01)

(52) U.S. Cl.
CPC .......... *A61B 5/4839* (2013.01); *A61B 5/0077* (2013.01); *A61B 5/165* (2013.01); *A61B 5/4519* (2013.01); *A61B 5/743* (2013.01); *A61B 2576/02* (2013.01)

(58) Field of Classification Search
None
See application file for complete search history.

(56) References Cited

U.S. PATENT DOCUMENTS

| | | |
|---|---|---|
| 6,358,917 B1 | 3/2002 | Carruthers et al. |
| 7,758,872 B1 | 7/2010 | Finzi |
| 2009/0028380 A1 | 1/2009 | Hillebrand et al. |
| 2009/0234175 A1* | 9/2009 | Maier ............................... 600/3 |
| 2010/0086215 A1* | 4/2010 | Bartlett .............. G06K 9/00335 382/197 |
| 2010/0329525 A1* | 12/2010 | Goodman ...................... 382/128 |
| 2013/0123647 A1* | 5/2013 | Bhatnagar et al. ........... 600/477 |

OTHER PUBLICATIONS

Shiffman et al. "Advanced Surgical Facial Rejuvinatin", springer-verlag Berlin Heidelberg 2012, chapter 4: "Muscles used in Facial Expressions", pp. 31-33.*

(Continued)

*Primary Examiner* — Katherine Fernandez
*Assistant Examiner* — Marjan Saboktakin
(74) *Attorney, Agent, or Firm* — Craige Thompson; Thompson Patent Law

(57) ABSTRACT

Apparatus and associated methods relate to method of determining a treatment plan with Botulinum Toxin (BT) and other procedures able to modify facial expressions, the method includes using a series of facial images of a patient eliciting various expressions to select individual expressive features as candidates for modification, the selected expressive features mapping to muscles that are used to create such expressive features, the muscles mapping into related expressive features of facial images of the patient eliciting different expressions, the related expressive features being weighted so as to provide further information used in determining an optimum treatment dosing for each treatment location. In an illustrative example, the method may include mapping the facial image of the patient to a model image using facial markers. In an exemplary embodiment, the method may advantageously provide a treatment that results in optimum expressive features as revealed in many different expressions.

17 Claims, 11 Drawing Sheets

(56) References Cited

OTHER PUBLICATIONS

Figure 1:
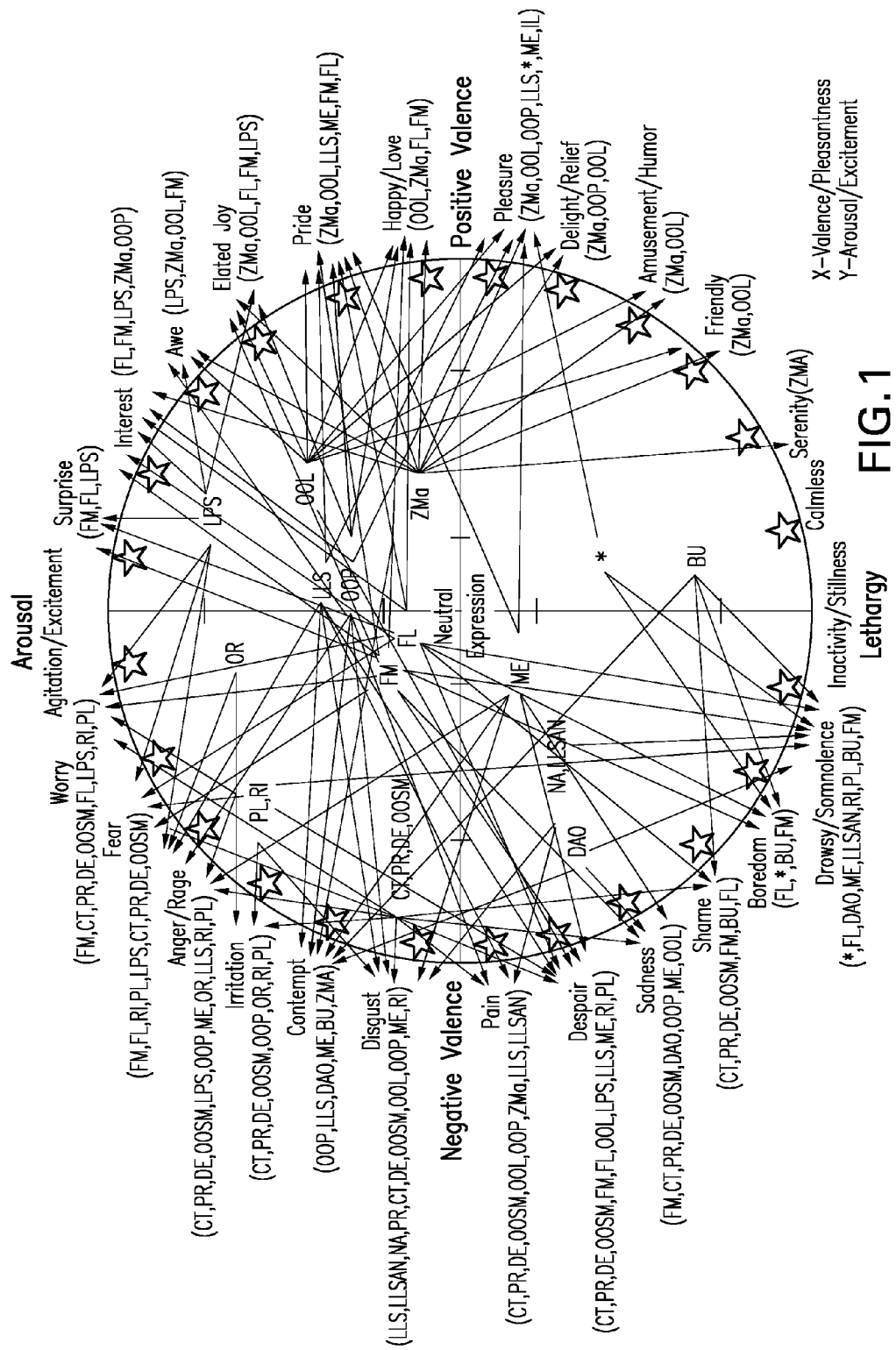

Murad Alam, et al., "Botulinum toxin and the facial feedback hypothesis: Can looking better make you feel happier?," J Am Acad Dermatol, Jun. 2008, pp. 1061-1072,vol. 58:6, US.
Lackey, et al., "Implications of botulinum toxin injection of the brow," J Am Acad Dermatol, May 2006, pp. 921-922, vol. 54:5, US.
Heckmann, et al., "Pharmacologic denervation of frown muscles enhances baseline expression...," J Am Acad Dermatol, Aug. 2003, pp. 213-216, vol. 49:2, US.
Carl-Herman Hjortsjo, "Man's Face and Mimic Language," 1969, 111 pages, Printed in Sweden.
Carruthers, et al., "Consensus Recommendations on the Use of Botulinum Toxin Type A in Facial Aesthetics" Plastic and Reconstructive Surgery, Nov Supp 2004, 22 pages, Vo. 114:6.
J. Charles Finn, et al., "Social Implications of Hyperfunctional Facial Lines," Dermatol Surg, May 2003, pp. 450-455 vol. 29:5, US.

\* cited by examiner

SYSTEM FOR MULTIDIMENSIONAL ANALYSIS, MODULATION AND OPTIMIZATION OF FACIAL EXPRESSIONS

BACKGROUND

In today's society, the face is essential for human communication, social interactions, facial feedback processes, signaling emotion and the perception of attractiveness and youthfulness. Scientists have long recognized the importance of facial expressions to communicate states of mind—this may include not only emotions, sensations, feelings, moods, personality traits and mental conditions, but also motivational, behavioral and cognitive processes.

Most people want to have pleasant and functional facial expressions in a modern social and communicative environment. Factors such as looking good for one's age, looking relaxed and natural, avoiding frozen looks, and maintaining a functional degree of facial animation are among those deemed desirable. Facial expressions play a big role in perceived physical attractiveness of a person, and people who are considered physically attractive receive preferential treatment in education, employment, medical care, legal proceedings, and romantic encounters that may result in greater happiness and success. The facial expressions of emotions are transmitted normally using static, dynamic, transient and permanent facial components.

However, both hyperactive (hyperfunctional) and hypoactive (hypofunctional) features of facial expressions can also transmit miscues about age, emotions, intentions and other mental states. In other words, facial expressions are central to human communication and the wrong facial expression can convey the wrong social message.

SUMMARY OF THE DISCLOSED TECHNOLOGY

Apparatus and associated methods relate to method of determining a treatment plan with Botulinum Toxin (BT) and other procedures able to modify facial expressions, the method includes using a series of facial images of a patient eliciting various expressions to select individual expressive features as candidates for modification, the selected expressive features mapping to muscles that are used to create such expressive features, the muscles mapping into related expressive features of facial images of the patient eliciting different expressions, the related expressive features being weighted so as to provide further information used in determining an optimum treatment dosing for each treatment location. In an illustrative example, the method may include mapping the facial image of the patient to a model image using facial markers. In an exemplary embodiment, the method may advantageously provide a treatment that results in optimum expressive features as revealed in many different expressions.

Various embodiments may achieve one or more advantages. For example, some embodiments may automate or semi-automate the generation of a BT treatment plan, alone or in combination with other agents and procedures able to modify facial features. In some embodiments, the generated treatment plan may optimally produce expressive features in response to a wide array of expressions. In an exemplary embodiment, the method may permit a physician of low-skill or modest experience to perform high-quality BT treatment on patients. For example, a physician with modest experience may treat a patient that might otherwise be referred to another more experienced physician. In some embodiments, the treatment dosages may be reduced due to the competing demands of the related expressive features. For example, a patient may desire a certain feature to be reduced while expressing fear, but may not desire to reduce a related expressive feature while expressing delight. An exemplary method may educate the patient, so that the patient feels that the treatment program is directed in part by the patient's own inputs.

BRIEF DESCRIPTION OF THE DRAWINGS

FIG. 1 is a graphical depiction of a spectrum of certain muscle activations that have been shown herein to occur frequently as functional facial expression components during the communication of certain emotions and mental states.

FIG. 2 is a decision tree for determining the degree of expression or activation intensity that can be applied to decoding both facial action elements (FEAMs) and gestalts (whole faces); relative to "baseline" (0%) and "maximum natural" (100%) activation.

FIG. 3 is a finer grained decision tree that in comparison with FIG. 2 can facilitate the description of more subtle differences between two slightly different facial expressions; reference is made to an intensity scale of facial components (FEAMs) and gestalt expressions of psycho-physiological states; relative to "baseline" and "maximum natural" activation.

FIG. 4 illustrates an analysis of the botulinum toxin (BT) effects producing a desired multidimensional shift in the perceptual signal values of the facial expressions mimicking the maximal facial expressions communicating emotions and psycho-physiological states; the perceptual signal values of the four best mimicking facial expressions of a female patient along each of the 8 different dimensions (emotion or psycho-physiological categories) before and after BT injections were reported by 3 observers; presented as averages of percentages relative to the maximal individual facial expressions of the corresponding emotion (100%).

FIG. 5 illustrates a block diagram of an exemplary botulinum toxin (BT) treatment system.

FIG. 6 depicts an exemplary top-level method for determining a BT treatment plan.

FIG. 7 depicts a flow-chart of an exemplary method of acquiring a set of facial images.

FIG. 8 depicts an exemplary method of identifying undesirable facial-expression activation markers.

FIG. 9 depicts an exemplary method of finding FEAMS associated with specific muscles or muscle groups.

FIG. 10 depicts an exemplary method for determining a treatment plan while considering competing or conflicting treatments for all treatment sites.

FIG. 11 depicts an exemplary method used in an exemplary BT treatment computer program.

Like reference symbols in the various drawings indicate like elements.

DETAILED DESCRIPTION

As used herein, the term "psycho-physiological state" means a condition experienced by a living being (whether communicated and/or felt) and which may result in a particular facial expression; including but not limited to worry, anxiety, fear, rage, anger, irritation, contempt, disgust, pain, despair, distress, sadness, shame, boredom, fatigue/somnolence, calmness, serenity, friendliness, amusement, relief, delight, pleasure, happiness, love, pride, elated joy, awe, interest, surprise, eyebrow flash greeting, novelty, expectation, goal attainment, power/control, external/internal standards disturbance or intrinsic pleasantness. Such meaningful conditions may be experienced by any animal, including, without limitation, mammals or humans. Thus, the methods herein may be, in certain embodiments, applied to any animal including, but not limited to, mammals or humans.

As discussed herein, a psycho-physiological state is considered "basic expressive" if it has characteristic static, dynamic or temporal activation patterns of Facial Expression Activation Markers (FEAMs) and/or muscles.

Facial Expression Activation Markers (FEAMs)

As used herein, the term "Facial Expression Activation Marker (FEAM)" means a basic static or dynamic topographic facial feature that cannot be further divided into smaller functionally meaningful components of facial expressions. A FEAM is an action element —an elementary facial feature whose intensity can be measured, but is otherwise a functionally indivisible anatomic and neuromotor facial component that can help an observer detect and form a hypothesis regarding the identity of the activated muscle(s) and mechanisms responsible for a particular facial expression.

FEAMs have been found herein to be the essential components of modern facial expressions that provide a common ground for multidisciplinary approaches to properly study and modulate human facial function, including communication of aesthetic mimetic and perceptual signals during the coding and decoding of human faces. That is, they are a "common denominator" that can be changed by various agents, procedures, and methods that can be used to modulate facial expressions—for example, laser surfacing can modulate FEAMs by remodeling and altering the properties of the facial skin, fillers can be used to decrease facial depressions or enhance elevations, while selective denervations of muscles (e.g., botulinum toxin, nerve ablations and surgical reconstructive methods) can target distinct sets of topographic FEAMs, but also alter distances between facial landmarks.

In certain embodiments herein, FEAMs can be grouped into functional "sets" based on muscle specificity (Table 1). In certain embodiments herein, each functional set comprises one or more FEAMs, and each functional set corresponds to a muscle activity characterizing a desired facial expression (Table 1; FIG. 1).

In certain embodiments, the methods herein are concerned with measuring the degree of expression or activation intensities of a FEAM. That is, a FEAM's degree of expression or activation intensity can be assessed (for example, visually and/or by palpation) according to criteria that are discussed herein. Automatic facial recognition programs able to quantitatively measure some FEAMs can also be used to determine the degree of FEAMs expression. In certain embodiments, a clinician will be able to assess the activation intensities of FEAMs and facial expressions of an individual. The facial expressions of basic expressive psycho physiological states (FIG. 1) can display both overlap and variations in the activation intensities of FEAMs and muscle activities between individuals and even within the same individual (left right facial asymmetry), suggesting that the ability to measure FEAM intensities as discussed herein is critical for the proper assessment and optimal modulation of FEAMs and facial expressions in a particular individual.

Thus, in certain embodiments, the present technology is directed to a method for achieving a desired facial expression on the face of a subject, the method comprising the steps of:

(a) measuring the activation intensity or intensities of one or more facial expression activation markers (FEAMs) of the subject for a desired facial expression;

(b) determining the activation intensity or intensities of one or more optimal FEAMs for the desired facial expression;

(c) grouping the one or more optimal FEAMs into one or more functional sets, each set comprising a desired optimal pattern of FEAMs and each set corresponding to a muscle activity characterizing the desired expression; and (d) applying an agent or procedure to the face, head or neck of the subject to implement the desired optimal pattern of FEAMs and corresponding muscle activity for the desired facial expression.

In certain embodiments, steps (a), (b) and (c) may include the production, evaluation, and optimization of full face displays and associated perceptual spaces characterizing multiple dimensions of psycho-physiological states, as will be discussed further herein.

Figure 2:
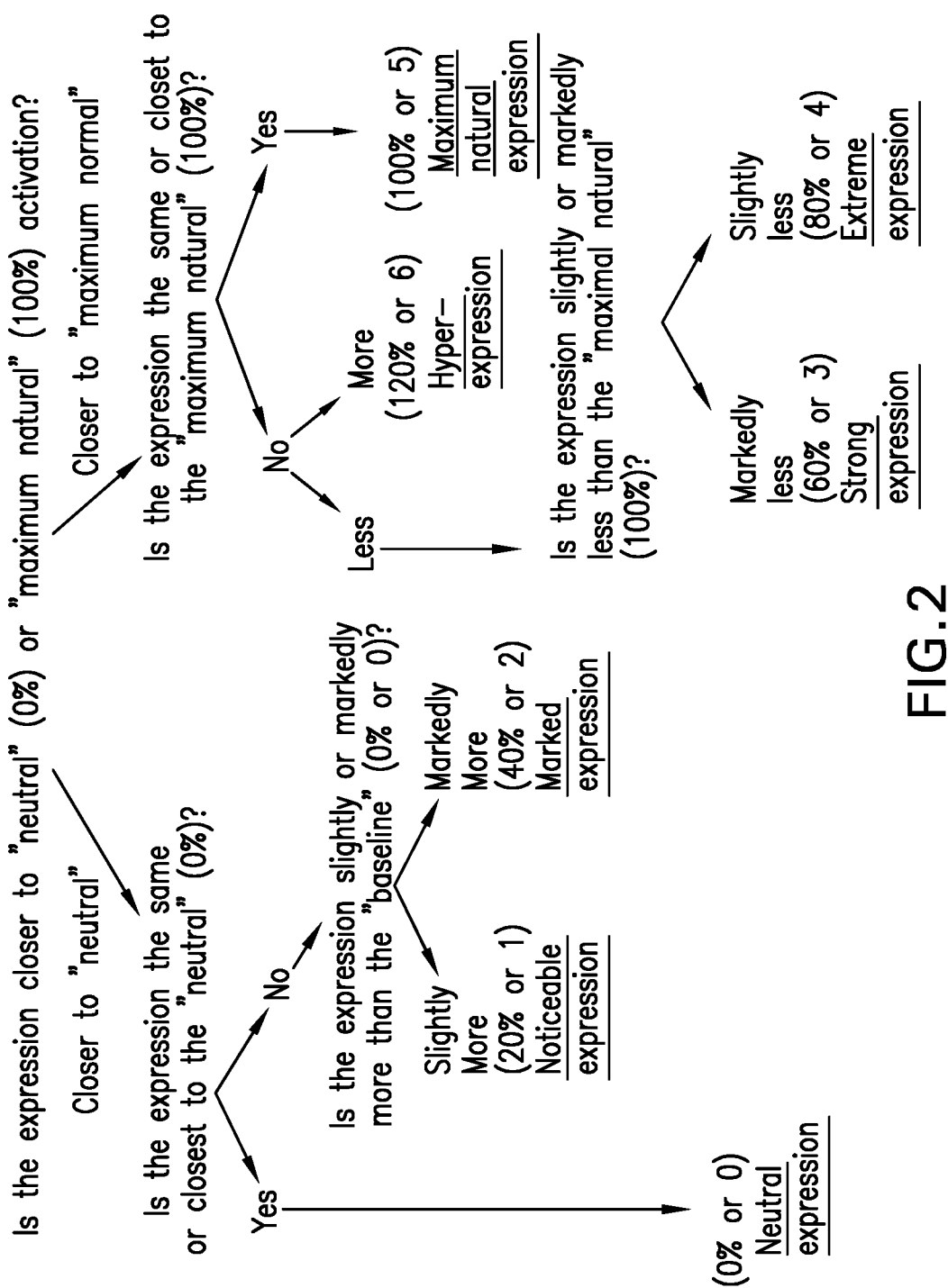

This evaluation is further discussed in FIG. 2, which presents a decision tree for determining the degree of expression or activation intensity that can be applied to decoding or assessing both facial action elements (FEAMs) and gestalts (whole faces)—of basic expressive psycho physiological states relative to 0% (baseline expression) and 100% (maximum natural activation of expression). In certain embodiments, the degree of expression or activation intensity can be presented as numeric gradations or as increments of, for example, 0% (baseline expression or activation), 20%, 40%, 60%, 80%, 100% (maximum natural activation) and 120% (hyperactivation). Due to the relatively large increments in gradations (20%) shown in FIG. 2, the decision tree shown therein can also be used to roughly assess FEAMs and facial expressions of basic expressive psycho physiological states relative to experience-derived internal standards or references (baseline 0% and maximum natural activation 100%) when recordings of the actual baseline (0%) and maximum natural activation (100%) are not available.

Figure 3:
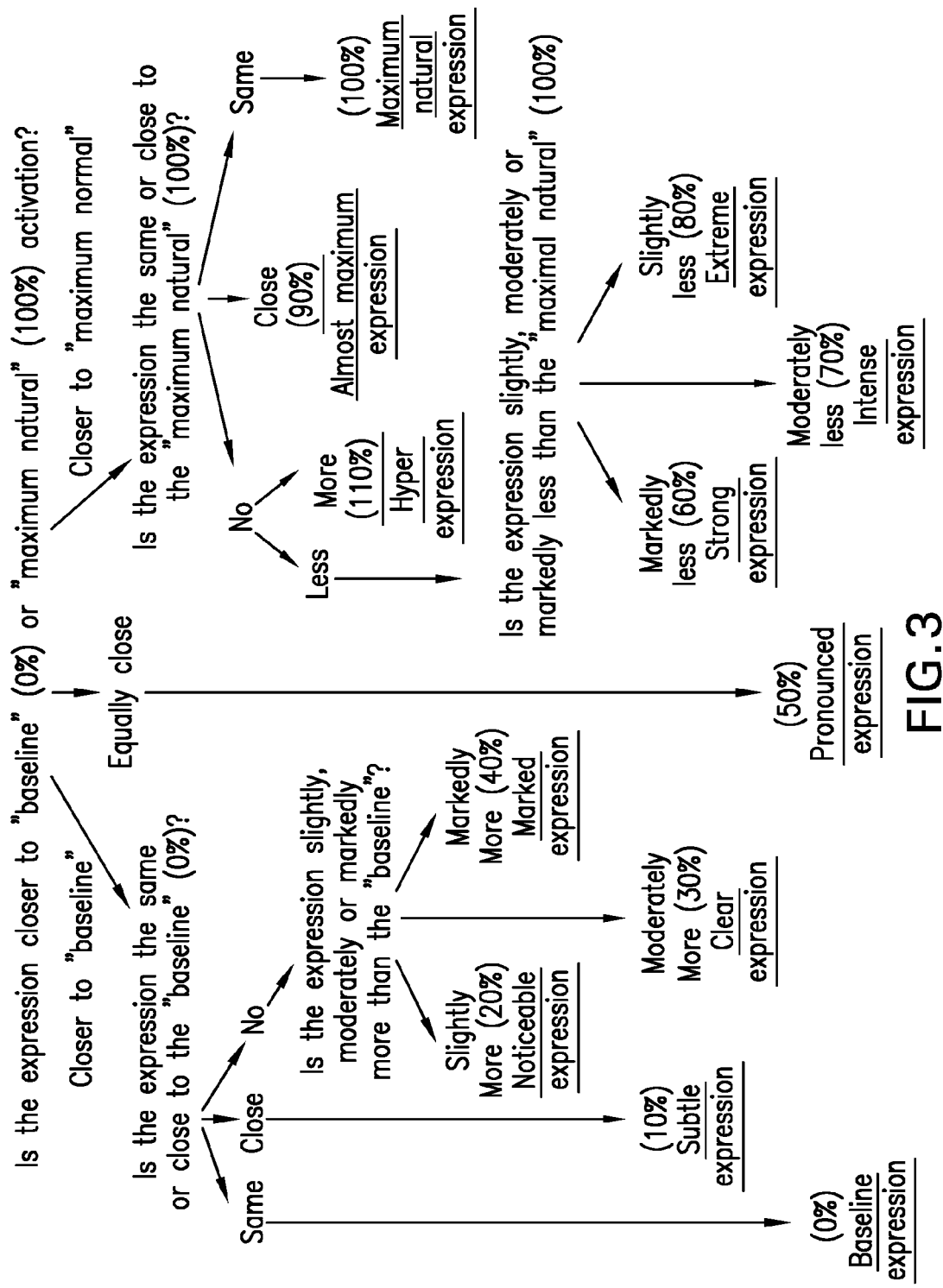

In FIG. 3, a finer grained decision tree (showing 10% increments) is presented; it allows observers to determine and document more subtle differences between two slightly different facial expressions of basic expressive psycho-physiological states or FEAMs. It is likely to help in detecting relatively small differences between two slightly different facial expressions when side by side comparison of the two facial expressions relative to recorded facial expressions illustrating baseline (0%) and maximum natural activation (100%) can be done.

Thus, in various embodiments, the determination of one or more optimal FEAMs for the desired facial expression comprises analyzing and testing the effects of FEAM changes on the facial expressions of two or more relevant psycho-physiological states.

SREDIC Intensity Scale

In certain embodiments, the methods herein include the application of the SREDIC Intensity Scale, which has herein been developed to determine and report the functional activation intensities of FEAMs organized by facial muscle specificity. As used herein, "SREDIC" refers to Specific feature, Relative distance, Elevations, Depressions, Interacting features and Coactivated distances.

As used in the methods herein, the "primary" FEAMs may help to formulate the functional hypothesis, and include the S (Specific features) and R (Relative distance) FEAMs; the "secondary" FEAMs E (Elevations) and D (Depressions) further confirm and refine the functional hypothesis; and the "tertiary" FEAMs I (Interacting features) and C (Coactivated distances) further expand or reformulate the functional hypothesis.

Primary FEAMs formulate the functional hypothesis. The primary topographic FEAMs are defined in certain embodiments of the methods herein as:

(i) Specific (S) or the most specific and unique topographic change or deformation resulting from a specified muscle activity, and (ii) Relative specific or unique distance (R) changes between specified facial landmarks.

The presence of any FEAMs that are specific and in general are not significantly shared or explained better by other co-occurring muscle activation can provide an important clue that a certain muscle activation is relevant to the examined facial expression. For example, vertical glabellar lines and decreased distance between eyebrows are produced most specifically by the corrugator muscles. Together with basic knowledge of functional anatomy, a clinician can formulate a muscle activity hypothesis as well as determine the possible types of muscle variants that might be present, for example, suggesting likely locations for the individual origins (bone attachments) of the activated muscle.

Functional splitting of the facial activations into surface topographic components (depression/elevation of surface facial features changing topographic shapes and forms) and into distance components (landmarks moving relative to each other in terms of relative distances, vector direction and angles) as described herein may be particularly helpful, since certain aesthetic procedures like laser ablations can erase surface topographic components while leaving the distance components and muscle activity largely intact. Similar natural variations in facial skin can also occur between different individuals. Topographical facial features may include, in various embodiments, elevations, depressions, shapes and relative distances between facial landmarks.

Examples of FEAMs can be seen in Table 1, where FEAMs associated with a muscle activity are presented in a sequential, modular, hierarchical fashion based on muscle specificity and organized by a functional evaluation of the individual face that starts in the middle of the upper face and moves laterally and then back to the middle of face and going down, and so on.

Secondary FEAMs further confirm and refine the functional hypothesis. Functionally relevant deformations in facial features overlying the trajectory of potential muscle activities are defined as secondary FEAMs, being the topographic facial elevations and depressions characteristic of a specific muscle activity and therefore confirming the functional hypothesis that a particular muscle or variant was activated during a particular facial expression. In certain embodiments, the secondary topographic FEAMs are presented in the current methods as surface deformations that can be observed visually and/or if possible by palpation (p). The secondary topographic features include:

(i) Elevations (E) that are surface deformations that are caused directly by the contracting muscle mass (e.g., superficial silhouettes or deeper muscle bulges) or their actions (bunches, etc.). Elevations can often be detected visually (or by palpation of contracted muscles whenever applicable in the area of the face (or neck) overlying the muscle perimeter and trajectory of muscle activities, and (ii) Depressions (D) that are surface deformations characteristically observed during particular muscle activities, such as lines, furrows, insertions in the skin tissue and other depressions overlaying the muscle perimeter and trajectory of muscle activities. Knowledge of the depressions derived from the insertions of the muscles in a particular facial location of a person can guide the locations of the treatments in that particular individual.

The secondary topographic deformations can occur in a characteristic form during isolated muscle activity or sometimes in an altered form in conjunction with other co-occurring topographic deformations from co-activated muscles. For example, deformation or decreased appearance of the corrugator depression may be due to co-activation of the frontalis during certain facial expressions like fear. Unusual deformations or presentations of the primary- and secondary topographic features can therefore be due to co-occurring muscle activities or can also be a clue to natural or artificially-induced variation.

Tertiary FEAMs further expand or reformulate the functional hypothesis. Many FEAMs are shared or distorted by other co-activated muscles, not being specific to a single muscle. Any such FEAMs related by anatomic proximity or functional interactions during a particular expression are defined in the current methods as tertiary topographic features. They include:

(i) Interacting (I) co-activated features such as shared topographic features with altered shapes and activation intensities due to co-activated muscles, and (ii) Coactivated distances (C) such as changes in distances between selected landmarks with alterations (deviations or distortions) in intensity activations due to interactions with functionally related co-activated muscles.

In certain embodiments, knowledge of common anatomic and neuromuscular variations can narrow down the mechanistic possibilities. Unusual deformations or presentations of the topographic features can be a clue to natural or artificially induced variation, or to other concurrent facial muscle co activations that further expand and refine the functional hypothesis. While the approximate location for common muscle and FEAM variants on the face is known based on functional anatomy knowledge including superficial insertions in the skin tissue and deeper attachments (e.g., to bones, etc.), more precise localization and identifications of variants in any given individual will also have to take into account the activation pattern of primary, secondary and tertiary features during particular facial expressions.

Quaternary facial features (FEAMs) are defined as individual permanent features that do not depend on muscle activations and often are not even in the areas adjacent to active muscles during facial expressions, including but not limited to scars, lesions, fat herniations, landmark shapes, hair color, eye color, etc. In certain embodiments, such characteristics related to individual appearance (for example, scars, growths, hair color and style) could be considered quaternary facial features and be added as descriptive codes at the end of scoring when they are visible for a particular facial expression, since they could also be hotspots of facial perception for observers. So, depending on purposes, such FEAMs might be specified individually at the end of coding for facial expressions and would provide more complete facial descriptions, but in general the reporting and modulation of facial expressions is more importantly connected to the activation patterns of the muscles and primary, secondary and/or tertiary FEAMs.

The SREDIC classification scheme discussed herein therefore organizes FEAMs according to muscle specificity based on Specific feature, Relative distance, Elevations, Depressions, Interacting features, and Coactivated distances (known herein interchangeably as the "SREDIC classification" or the "SREDIC Intensity Scale" as shown in Table 1), and in certain embodiments provides the basis for reporting differential patterns of activation intensities for FEAMs and associated muscles during facial expressions, using the Intensity Scale criteria shown in FIG. 2.

In certain embodiments, the SREDIC Intensity Scale (as shown in FIG. 2) includes a numerical intensity activation scale of facial expressions (FEAMs or full facial expressions of psycho-physiological states) with 6 normal gradations (0, 1, 2, 3, 4, 5) and corresponding percentages relative to neutral (0 activation) and maximum natural activation (100% or 5):

0—no activation or neutral, with expression activation closer to 0%.

1—trace, barely noticeable or subtle activation, with expression activation closer to, in various embodiments, about 10 to about 25%, or about 15% or about 20%.

2—marked activation or clearly visible with expression activation closer to, in various embodiments, about 25% to about 45%, or about 30% or about 40%.

3—strong or pronounced activation, with expression activation closer to, in various embodiments, about 45% to about 70%, or about 50% or about 60%.

4—extreme activation with expression activation closer to, in various embodiments, about 70% to about 90%, or about 75%, or about 80% or about 90%.

5—maximum natural activation or natural apex activation, with facial expression activation close to, in various embodiments, about 90% to about 100%, or about 95% or about 100%.

In certain embodiments, a seventh gradation (6) can be useful to signal hyperactivation (hyperexpression) or stimulated activation that is clearly noticeable beyond the natural maximum expression, sometimes possibly due to a condition or procedure that has altered the facial expression activation beyond the natural maximum, with facial expression activation closer to, in various embodiments, about 110%, about 115%, about 120%, about 130% or about 150%.

In certain embodiments, "U" can be added as a descriptive code to signal Uncertainty or to note justified disputes when separate evaluators disagree on the presence or absence of very subtle, transient, uncertain or hard to detect features. With the SREDIC system, the observers (or, in certain embodiments, automated system(s)) that use the current scale are presumed to be able to detect activation intensities of markers within a certain margin of error. The exact margin of error would vary based on the actual ability of observers or automated systems to detect activated features. "U" therefore may be used to signal uncertainty that a FEAM or muscle was in fact activated.

In certain embodiments, "X" can also be added if necessary to the of coding for part of a facial expression to signify that activation intensities for specified FEAMs or muscles could not be evaluated or examined, due to shadows, poor visibility, etc.

In certain embodiments, tertiary FEAMs can be reported using the SREDIC Classification by specifying the coactivated muscles for a particular FEAM, but in certain embodiments they would have no intensity. In certain embodiments, quaternary FEAMS or other descriptive features can also be added at the end of the coding, but in certain embodiments they would also have no intensity. The SREDIC classification and assessment therefore allows a functionally meaningful, modular reporting of detailed personal facial features that is based on muscle specificity.

For example, to illustrate the modular reporting of the SREDIC classification and assessment (Table 1, FIG. 2) of the facial features changed by LLSAN muscle activity during the facial expressions of disgust, one can choose to report and compare only the intensity for the most specific (primary) FEAMs for LLSAN: for the left side of the face of the first person (L)E1:LLSAN-S(80%),R(80%) and for the left side of the face of a second person (L)E2:LLSAN-S(60%),R(60%). In other instances, a more detailed SREDIC scoring and facial analysis, based on Table 1 and FIG. 2, would reveal for the same two expressions:

(L)E1:LLSAN-S(80%),R(80%),
E(a80%,b20%,c60%,d60%,e60%,p60%),
D(a20%,b40%,c40%,d80%,e60%,f80%,g20%,h80%, i80%,j60%),
I(a20%PR+40%CT+20%OOSM+20%DE,b20%PR+ 20%DE+20%OOSM,c40%O O,d20%NA+,e40%OOP+ 40%OOL+ 40%ZMA,f20%NA,g20%NA+40%OOL+40%ZMA, h0%,i40%ZMA)
C(a20%PR+40%CT+20%OOSM+20%DE,b40%OOP+ 40%OOL+40%ZMA,c0%,d40%ZMA+e0%+f0%+ g40%ZMA); and (L)E2:LLSAN-S(60%),R(60%),
E(a40%,b40%,c40%,d40%,e40%,p40%),
D(a20%,b20%,c40%,d40%,e20%,f40%,g20%,h60%, i80%,j60%),
I(a40%PR+40%CT+40%OOSM+20%DE,b40%PR+ 20%DE+40%OOSM,c40%O O,d40%NA,e40%OOP, f40%NA,g40%NA+40%LLS, h0%, i40%LLS),
C(a40%PR+40%CT+40%OOSM+20%DE,b40%OOP+ 40%LLS,c40%LLS,d40% LLS+e0%+f0%+g40%LLS);

This particular type of modular and hierarchical facial analysis is unique in terms of both the level of detail and usefulness for anybody trying to analyze, optimize and modulate the FEAMs of individual facial expressions.

The present technology relates, in certain embodiments, to the systematic and comprehensive assessment, measurement, analysis, production, modulation and/or optimization of individual facial expression patterns in terms of intensity activation patterns of individual FEAMs and corresponding muscles. The current technology combines a dimensional model of Core Affect Circumplex with further cognitive maturation and differentiation into discrete emotion schemes, emotional dimensions and individual functional facial expression patterns of psycho-physiological states, providing the basis for a novel comprehensive approach to analyzing, producing, optimizing and/or selectively modulating the individual facial components and displays of expressive psycho-physiological states.

In certain embodiments, the technology herein provides methods and systems that better do any one or more of the following: detect, analyze, extract, classify, measure, compare, interpret, report, produce, selectively modulate or optimize facial expression markers during inter- and intra-personal signal communication of basic expressive psycho-physiological states. In certain embodiments, the methods and systems herein also provide reproducible means to detect and reveal in sufficient detail the key differential, interacting and shared functional anatomic elements and patterns of whole face expressions necessary to guide and/or assist interested clinicians to safely assess, optimize and/or change facial expressions in a balanced manner that is faithful to individual human anatomic, functional and aesthetic principles, and that optimizes human communication and wellbeing.

The methods herein contemplate applications incorporating any approach, procedure or agent able to change facial expressions; for example, applying any agent capable of modifying an FEAM or applying any procedure that includes the step of modifying an FEAM. Any such agent may be applied to the subject's body, for example, to the face, head or neck topically or by injection.

As an example, in certain embodiments, the methods herein contemplate the use of botulinum toxin and hyaluronic acid modulation and optimization of facial displays during basic emotion and other psycho-physiological states. Certain case studies herein discuss optimized selective targeting with botulinum toxin (BT) injections of the activation intensity patterns of FEAMs and muscles characteristic of the individual prototypic expression of emotions such as, among other conditions, fear. That is, in certain embodiments, the methods herein contemplate the implementation of desired muscle activity in a way that includes partial or complete paralysis of a muscle located in the subject's body, for example, within the subject's face, head or neck.

As used herein, the term "BT" means botulinum toxin in any commercially available form for cosmetic and medical purposes, such as, for example, the product owned and sold by Allergan, Inc. under the trademark Botox®. In certain embodiments, the methods herein can be applied to optimize various medical, surgical, reconstructive, aesthetic and other selective approaches (including but not limited to procedures like BT and filler injections).

The methods herein allow comprehensive quantitative analysis, optimization and selective balanced changes of human facial features and their perceptions in a functionally relevant way, during facial expressions of multiple basic emotions and other meaningful normal expressive psycho-physiological states. Quantitative methods are discussed; these are based on indivisible functional anatomic elements of facial expressions.

The methods described herein also include, in various embodiments, the elicitation, collection, measuring, optimization or modulation of the Individual Prototypical Facial Expressions of basic expressive psycho-physiological states in terms of activation intensity patterns of FEAMs and muscles in the whole face as maturing and differentiating mimetic signals branching along the corresponding psycho-physiological dimensions of an Individual Facial Expression Circumplex (IFEC). The IFEC has been developed herein, and is based on Individual Maximal Facial Prototypes of Psycho-Physiological States, also described herein, that are organized around the affect circumplex. It has been found herein, that unique to the art, the Individual Facial Prototypes of emotions for any given individual usually falls within the muscle activation sets described in FIG. 1, which correspond to the muscle activations also frequently observed by others during the facial expressions for the corresponding emotion or psycho-physiological state. The personal intensity activation pattern of FEAMs and corresponding muscles characterizing each Individual Prototypical Facial Expression of psycho physiological states can be elicited, measured, reported, modulated and optimized more precisely based on direct observation and SREDIC analysis.

The perceived mimetic signal values of modulated faces can then be further evaluated and optimized in terms of reported shifts in the multidimensional perceptual spaces based on the measurements of perceived signal coordinates along the dimensions of the Facial Expression Circumplex of psycho-physiological states.

Functional Sets

In certain methods herein, the activation intensities of the FEAMs may be reported in a hierarchical and modular fashion into the one or more functional sets based on muscle specificity. This may be done to facilitate the determination of both unique FEAMs present during a particular muscle activation and FEAMs shared with other co-activated muscles and facial expressions of the IFEC. Specifically, in certain embodiments the activation intensities of the FEAMs are grouped into one or more functional sets based on muscle specificity of changes in topographic facial features. These functional sets may facilitate the determination of both unique FEAMs present during a particular muscle activation and FEAMs shared with other co-activated muscles- and facial expressions, which help to determine and optimize which personal facial expressions of the IFEC will be affected by changes in specific FEAMs and muscle activity.

Thus, as an example, a clinician can report FEAM activation intensity measurements and SREDIC analysis for a facial expression of an individual to assess and report activation intensity patterns for the facial features of a patient, either by observing the face, photographs or other digital recordings. The facial expressions of basic expressive psycho physiological states can show intra individual asymmetry and inter individual variation in the activation intensity patterns of FEAMs during the facial expression of, e.g., disgust. This illustrates the need for the more precise and personalized method of SREDIC to describe, analyze, optimize and/or modulate the intensity of elementary components (FEAMs) of facial expressions.

Turning now to the Figures, FIG. 1 shows a spectrum of certain muscle activations that have been shown herein to occur frequently as functional facial expression components during the communication of certain emotions and mental states. The following muscle abbreviations are used throughout the present disclosure: Buccinator (BU), Corrugators Corrugator Supercilli (CT), Depressor Anguli Oris (DAO), Depressor Labii Inferioris (DLI), Depressor Supercilli (DE), Depressor Septi Nasi (DS), Frontalis Corrugators (CT), Frontalis, Medial Frontalis (FM)—Frontalis, Lateral (FL), Incisive Labii—superioris and inferioris (IL), Levator Anguli Oris (LAO), Levator Palpebrae Superioris (LPS), Levator Labii Superiorii (LLS), Levator Labii Superiorii Aleque Nasi (LLSAN), Mentalis (ME), Nasalis transverse (NA), Orbicularis Oculi, Lateral (OOL), Orbicularis Oculi (OO), Orbicularis Oculi Lateralis (OOL), Orbicularis Oculi Nasal (OON), Orbicularis Oculi, Palpebral (OOP), Orbicularis Oculi—Superior Medial (OOSM), Orbicularis Oris (OR), Orbicularis Oris Marginalis (ORM), Orbicularis Oris Peripheralis (ORP), Platysma (PL), Procerus (PR), Risorius (RI), Zygomaticus Major (ZMa), Zygomaticus Minor (ZMi). The following 4 facial zone abbreviations are used throughout the present disclosure: Z1 zone 1 extends between vertical lines from mid face to inner canthus; Z2 zone 2 from inner canthus to mid pupil; Z3 zone 3 from mid pupil to outer canthus; Z4 zone 4 from outer canthus to anterior ear).

In FIG. 1, the asterisk "*" denotes that relaxation (not contraction) of LPS is present. The muscles activated during prototypical facial expressions of basic emotions were supplemented with those observed experimentally to occur more frequently during the facial expressions of other expressive psycho-physiological states.

Variant configurations, intensities, sequences and partial displays of modal facial expressions of basic psycho-physiological states may be produced during personal differentiation and contexts, suggesting a need for the elicitation, elucidation and SREDIC analysis of Individual Maximal Facial Prototypes of Psycho Physiological States that are individually meaningful modal facial expressions and intensity activation patterns of FEAMs characteristic for each selected emotion, mental and psycho-physiological state.

In certain embodiments, the changes in the facial expressions of the relevant psycho-physiological states are differentiated along the dimensions of a graph having an x axis and a y axis. In certain embodiments, the x axis represents valence (pleasantness) and the y axis represents arousal (excitement).

Table 1 shows an illustration of the SREDIC Classification System, which has herein been developed. As discussed herein, the SREDIC system is a modular hierarchical and functional classification system that can be used to partially or comprehensively report and analyze the activation intensity of FEAMs grouped under corresponding muscles. The x-axis of the table includes FEAMs presented hierarchically based in muscle specificity such as, e.g., specific or unique changes, relative distances, elevations, depressions, interacting coactivated features and coactivated distances. For each muscle, Table 1 presents examples of corresponding FEAMs organized such as, e.g., Specific or unique change, Relative Distance, Elevations, Depressions, Interacting Coactivated Features and Coactivated Distances.

TABLE 1

Illustration of the SREDIC Functional Classification System of facial features based hierarchically on muscle specificity (FEAMs), with examples of FEAMs grouped modularly under corresponding muscles:

| FEAMs | Specific or unique changes (Primary FEAMs) | Relative distances (Primary FEAMs) | Elevations (Secondary) | Depressions (Secondary) | Interacting coactivated features (Tertiary) | Coactivated distances (Tertiary) |
|---|---|---|---|---|---|---|
| Topographic Facial Expression Activation Markers or Action Elements | Most specific or unique feature change characterizing each muscle activity such as lines, bulges, etc. | Most specific or unique change in relative distances between selected facial landmarks | Silhouettes, bulges or bunches from muscles observed visually or by palpation overlaying the trajectory of the muscle activity | Depressions from activated muscles present as lines, furrows, depressions, poaches, insertions overlaying the trajectory of the muscle activity | Shared features with altered shapes and activation intensities due to co-activated muscles | Changes in distances between selected landmarks with alterations (deviations) in activation intensities due to co-activated muscles |
| Muscles | | | | | | |
| FM | (a)Increase in transverse (horizontal) medial forehead lines (frontal furrows) in Z1 | (a) Increase in the vertical distance between the medial eyebrow and the inner canthus | Transverse medial forehead bulges and bunches (moving upwards) in the region from above the eyebrows to galea aponeurotica in: (a)Z1 (b)Z2 (p)May be palpable with activation (moving upwards) in the Z1 and Z2 regions of the forehead | Transverse medial forehead lines between the galea aponeurotica and eyebrows in: (a) upper Z1 transverse frontal furrows (b) Z2 transverse frontal furrows; (c) lower Z1 (supraglabellar furrow) (d) Smoothing of the glabellar region with upward pull (e) Stretching of raising medial cover (cover fold and revulsion margin of coverfold) of upper eyelid (f) Narrowing of the nose root (g) Deepening of medial infraorbital furrow Note: Shape of the transverse forehead lines can give away the type of frontalis variant being present | (a) Attenuation of transverse medial frontal FM furrows (lines) with PR, OOSM and/or DE co-activation (b) Attenuation of transverse lateral Z2 frontal FM lines with CT co-activation (c)Increase in lateral transverse FM lines in Z2 if FL co-activation is present (d) Increase in supraglabellar furrow in Z1 with increased bunching from CT co-activation (during the omega sign) (e) Attenuation of A-type FM eyebrow with co-activation of PR, OOSM, DE or LLSAN towards a V-type eyebrow (f) ) Stretching of raising medial cover of upper eyelid by FM is increased by co-activated FL (g) Stretching of raising medial cover of upper eyelid by FM is | (a) Further increase in distances between the medial eyebrow and inner canthus with synergistic FL co-activation (b) Increase in the vertical distance between the medial eyebrow and inner canthus is attenuated (or reversed) by opposing CT, PR, OOSM, DE or LLSAN co-activation |

TABLE 1-continued

Illustration of the SREDIC Functional Classification System of facial features based hierarchically on muscle specificity (FEAMs), with examples of FEAMs grouped modularly under corresponding muscles:

| FEAMs | Specific or unique changes (Primary FEAMs) | Relative distances (Primary FEAMs) | Elevations (Secondary) | Depressions (Secondary) | Interacting coactivated features (Tertiary) | Coactivated distances (Tertiary) |
|---|---|---|---|---|---|---|
| | | | | | decreased by co-activated CT, PR, OOSM, DE, LLSAN (h) Narrowing of the nose root can be attenuated (or reversed) by PR, DE, OOSM, and LLSAN (i) Upward indirect pull by FM on upper medial corner of infraobital triangle can be enhanced by co-activated LLSAN, LLS, ZMI, ZMa (j) Upward indirect pull by FM on upper medial corner of infraobital triangle can be decreased by co-activated CT, PR, OOSM, or DE | |
| PR | (a)Increase in horizontal line(s) (transverse furrows) over the nasal root with downward movement of the glabella | (a)Distance between the medial eyebrow and inner canthus decreases | (a)Bulge or silhouette (downward movement) in the glabellar region between eyebrows (b) Horizontal bunches (downward movement) on the upper dorsal bridge of the nose (c)Medial part of the upper eyelid cover fold (and revulsion margin of cover fold) lowering (downwards movement) (d) Broadening of the nose root (horizontally) (p)Palpable in the glabellar and nasal root region with activation (moving downwards) | (a)Supraglabellar depressions (insertions) at the superior margin of the contracted procerus (b)Oblique (A-type) glabellar and nasal orbital lines (c)Horizontal line(s) on the root of the nose (most depressed part of the dorsal nasal ridge, superior to the line formed by the inner canthi) (d)Horizontal line(s) on the lateral nasal bridge (nasal sidewalls) and nasal-orbital (superior medial orbital wall) horizontal lines above the line formed by the inner canthi (e)Horizontal line(s) on the dorsal bridge at (or inferior to) the line formed by the inner canthi | (a)Oblique (A-type) glabellar and nasal orbital lines increased by co-activated CT, OOSM, DE (b) PR increase in V-eyebrow can be decreased by activation of FM (c) PR increase in V-eyebrow can be enhnaced by co-activation of CT, OOSM, DE (d) Lowering of the medial cover of the upper eyelid by PR can be decreased by co-activated FM and FL (e) Lowering of the medial cover of the upper eyelid by PR can be enhanced by co-activated CT, OOSM, DE (f)Horizontal line(s) on the upper dorsal nose (nasal root) can appear enhanced by superior downward bunching from CT co-activation (g)Decrease in horizontal PR lines across the nasal root (radix) and bridge with co-activation of FM | (a) The decreased distance between the medial eyebrow and inner canthus is attenuated by opposing co-activated FM or FL (b) Distance between the medial eyebrow and inner canthus decreases further with co-activated CT, DE, OOSM |

TABLE 1-continued

Illustration of the SREDIC Functional Classification System of facial features based hierarchically on muscle specificity (FEAMs), with examples of FEAMs grouped modularly under corresponding muscles:

| FEAMs | Specific or unique changes (Primary FEAMs) | Relative distances (Primary FEAMs) | Elevations (Secondary) | Depressions (Secondary) | Interacting coactivated features (Tertiary) | Coactivated distances (Tertiary) |
|---|---|---|---|---|---|---|
| | | | | | (h) Horizontal PR line(s) on the lateral nasal bridge and nasal-orbital sidewall (superior medial orbital wall) above the line formed by the inner canthi can occur with co-activated CT, DE, OOSM<br>(i) Broadening of the nose root by PR can be enhanced by DE, OOSM, and LLSAN<br>(j) Broadening of the nose root by PR can be decreased by activated FM<br>(k) Horizontal line(s) on the lateral nasal bridge and nasal orbital (medial inferior wall of the orbit) lines at (or below) the line formed by the inner canthi can be enhanced by co-activated LLSAN | |
| CT | (a) Increase in vertical glabellar line(s) between eyebrows | (a) Decreased horizontal distance between medial eyebrows | (a) Horizontal bunching raising inferior to the supraglabellar furrow(s)<br>(b) Vertical glabellar bunches moving medially in Z1<br>(c) Bulges above the medial eyebrows in Z2<br>(d) Upper eyelid cover fold lowering in Z2<br>(e) Lateral upper eyelid cover fold lowering in Z3 with inferior medial pull<br>(p) Palpable with activation (moving medially) in the Z1 and Z2 regions of the inferior forehead and eyebrows | (a) Horizontal supraglabellar furrow(s) in Z1<br>(b) Vertical glabellar lines in Z1<br>(c) Oblique (A-type) glabellar and nasoorbital lines in Z1<br>(d) Parenthesis-like (ripple-like) fine lines above eyebrow in the middle and lateral Z2 inferior forehead<br>(e) Angular (or triangular) depression above eyebrow in the middle and lateral Z2 inferior forehead<br>(f) Parenthesis-like (ripple-like) fine lines above eyebrow extending into medial Z3<br>(g) Angular (or triangular) depression above eyebrow | (a) Increase in supraglabellar horizontal furrows from CT bunching can be further increased and extended laterally with co-activation of FM and FL<br>(b) Increase in supraglabellar horizontal furrow(s) from CT bunching can be decreased by PR, DE and LLSAN<br>(c) Attenuation of angular (or triangular) depression above eyebrow on inferior forehead (mid-lateral Z2 and medial Z3) with FL co-activation<br>(d) Attenuation of parenthesis-like fine lines on the inferior forehead (mid-lateral Z2 and medial Z3) with FL co-activation<br>(e) Further increase and upward elongation of CT | (a) Attenuation of the CT decrease in the distance between the upper eyebrow (above the lacrimal papilla of the lower eyelid margin) and the inner canthus in the presence of decreased distance between eyebrows by CT suggests concurrent co-activation of the opposing FM or FL<br>(b) Further decrease in the distance between the upper eyebrow (above the lacrimal papilla of the lower eyelid margin) and the inner canthus with co-activated PR, OOSM, and DE<br>(c) Decrease in the distance between the revulsion margin of upper eyelid cover fold and intercanthal (inner-outer canthal) distance in Z2 and Z3 by CT is attenuated by co- |

TABLE 1-continued

Illustration of the SREDIC Functional Classification System of facial features based hierarchically on muscle specificity (FEAMs), with examples of FEAMs grouped modularly under corresponding muscles:

| FEAMs | Specific or unique changes (Primary FEAMs) | Relative distances (Primary FEAMs) | Elevations (Secondary) | Depressions (Secondary) | Interacting coactivated features (Tertiary) | Coactivated distances (Tertiary) |
|---|---|---|---|---|---|---|
| | | | | extending into medial Z3 | vertical glabellar lines with co-activation of FM (f) Further increase and downward elongation of CT vertical glabellar lines with co-activated PR, OOSM, and DE (g)Oblique (A-type) nasorbital CT lines can be deepened by common co-activation of PR, OOSM, and DE (h)Further lowering of the medial eyebrow in Z1 from PR, OOSM, DE and LLSAN coactivation (i)Further lowering deformation of eyebrow in Z2 from co-activated OOSM (j)Further lowering of the upper eyelid cover fold in Z2 and Z3 by co-activated OOSM and OOL (k) Lowering of the the upper eyelid cover fold in Z2 and Z3 by CT can be attenuated by co-activated FM and FL | activated FM and FL (d)Further decrease in the distance between the revulsion margin of upper eyelid cover fold and intercanthal distance in Z2 and Z3 with co-activated OOSM and OOL |
| LLSAN | (a)Depression between the alar crease and upper nasolabial fold immediately lateral to the nose sharply deepened by superior medial pull | (a)Decreased distance between the upper part of the nasolabial fold and the inner canthus | (a)Transverse bunches on the nasal bridge (b)Oblique bunches (V-type) on the dorsal nasal bridge (c) Nasal-orbital (medial inferior orbital sidewall) bunches(V-type) and bulges raising with the superior medial part of the infraorbital triangle (d)Bunches raising above the lower eyelid crease (furrow) (e)Bunches above the infraorbital crease (furrow) with raising of | (a) Horizontal line(s) on the dorsal nasal bridge (ridge) (transverse dorsal nose furrows) (b) Horizontal lines nasal-canthal and nasal-orbital (medial orbital sidewall) (c) Oblique (V-type) lines on the dorsal nasal bridge (d)Oblique (V-type) nasal-orbital (medial inferior wall of the orbit) and nasal-canthal lines (e)Deepening of the lower eyelid crease (furrow) (f)Wrinkling or deepening of the infraorbital | (a)Oblique (A-type) glabellar and nasal-orbital (medial superior orbital sidewalls) bunches and lines enhanced by common coactivation of PR, CT, OOSM, DE (b)Horizontal lines (furrows) on the nasal root, nasal-orbital and nasal-canthal lines enhanced by common co-activation of the PR, DE, OOSM (c)Oblique (V-type) nasal-canthal and nasal-orbital (medial inferior orbital wall) lines enhanced by OO (d) Oblique (V-type), oblique-vertical and naso-alar lines on the nasal dorsum and | (a)Decreased distance between the medial eyebrow and inner canthus due to common co-activation of PR, CT, DE, and OOSM (not seen if frontalis is activated) (b)Decreased distance between lower eyelid margin and intercanthal line by LLSAN pushing lower eyelid up can be further decreased by co-activations of OOP, LLS, OOL, and ZMa (c)Further decreased distance between the upper part of the nasolabial fold and the inner canthus with co-activation of LLS (d)Decreased |

TABLE 1-continued

Illustration of the SREDIC Functional Classification System of facial features based hierarchically on muscle specificity (FEAMs), with examples of FEAMs grouped modularly under corresponding muscles:

| FEAMs | Specific or unique changes (Primary FEAMs) | Relative distances (Primary FEAMs) | Elevations (Secondary) | Depressions (Secondary) | Interacting coactivated features (Tertiary) | Coactivated distances (Tertiary) |
|---|---|---|---|---|---|---|
| | | | the infraorbital triangle (p)Palpable with activation (moving upwards) between the frontal process of maxilla (superior part) and nasal alae, with the lateral part (strand) inserting in the upper lip | crease (furrow) (g)Vertical and nasoalar lines on the nasal dorsum and sidewalls (h) Depression between the alar crease and upper nasolabial fold immediately lateral to the nose sharply deepened by superior medial pull (i) Deepening of the alar nasal crease and nostril dilatation with pulling up the wing of the nose (j) Flattening of the philtral columns and Cupid's bow with pulling of of the upper lip up | sidewalls enhanced by co-activated NA (e)Deepening of the lower eyelid crease and infraorbital crease by OOP, LLS, ZMi, ZMa, OOL (f)Deepening of the alar nasal crease with medial superior extension enhanced by NA (g)Upper nasolabial fold can be further increased by NA, LLS, LAO, OOL, ZMI, ZMA (h) Upper lip elevation and increased mucosal upper lip show can be decreased by opposing activation of ORP or ORM (i) Upper lip elevation and increased mucosal upper lip show can be increased by LLS and ZMa | distance between the inner canthus and the upper margin of the upper lip can be further decreased by LLS and ZMa (e)Decreased distance between the inner canthus and the upper margin of the upper lip can be attenuated by activation of ORP or ORM (f)Show of upper teeth(vertical distance of the shown teeth) under the lateral nasal ala is decreased or obliterated by opposing co-activation of ORP or ORM (g)Show of upper teeth under the lateral nasal ala (vertical distance of the shown teeth) can be increased by co-activated LLS and ZMa |

By allowing a balance of personal mimetic differentiation with perceptual and aesthetic goals, in certain embodiments the present methods facilitate facial modulating approaches to beneficially and optimally change facial expressions of psycho-physiological expressive states and related intra- and inter-personal signals by any one or more of the following:
(1) evaluating, determining and facilitating the production of optimal individual activation intensity patterns of FEAMs and muscles based on targeting of the prototypical facial features and expressions characteristic of basic expressive psycho-physiological states;
(2) predicting and measuring selective relative shifts in the perception of modulated facial features and expressions along the circumflex coordinates of valence (x axis, pleasure-displeasure continuum), arousal (y axis, inactivity-tension continuum) and other dimensions of psycho-physiological states to determine the optimal corresponding activation patterns of FEAMs and muscles; and
(3) selectively and/or quantitatively modulating specific intensity activation patterns of static, dynamic or temporal FEAM(s) and muscle(s) to facilitate production of novel optimal facial expressions, as well as future identification of associated functional changes in perception, aesthetics, mimetic differentiation, psycho-physiology, psycho-pathology, cognition, neuroanatomic plasticity or other important signals associated with human communication and nature.

Figure 4:
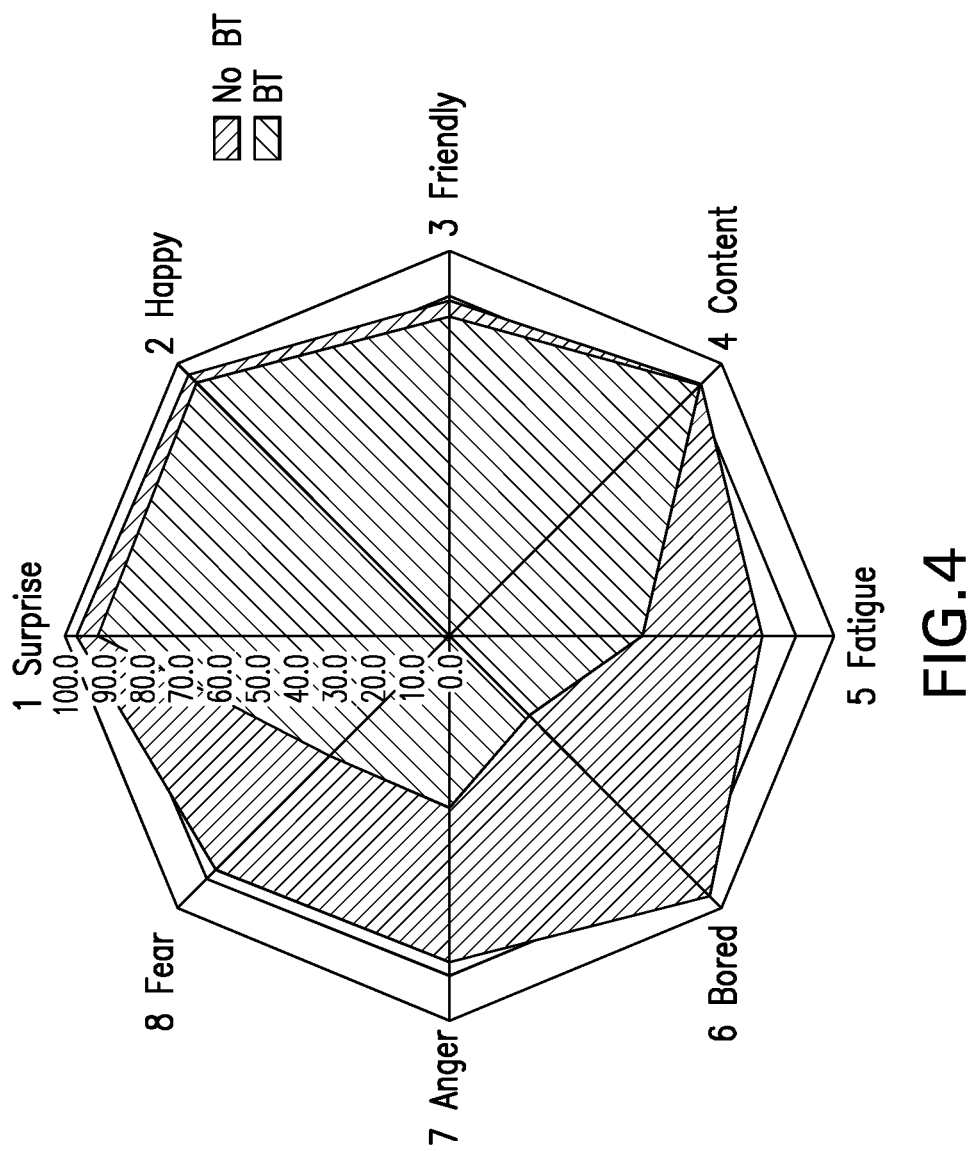

The multidimensional effects on modulated facial expressions and observers' perceptual spaces are further illustrated in a case study through optimized selective targeting with BT injections of the activation intensity patterns of FEAMs and muscles characteristic of the individual prototypic expression of fear (FIG. 4).

EXAMPLE 1

A 35 year old Caucasian woman with no significant past medical history complained of undesirable facial features during facial expressions that she believed conveyed negative emotions to others, including unpleasant features and overexpression of lines in the forehead, glabella and mouth regions. The patient reported these bothersome features to be barely noticeable at rest, but becoming significant during certain facial expressions Like many patients seeking treatment with BT for hyperkinetic features, the patient wished to enhance her facial appearance while being able to maintain some functional ability to communicate meaningful facial expressions of basic emotions, wanting to avoid a "frozen" facial appearance after the treatment.

Multidimensional testing for functional facial expressions was conducted as described in the current disclosure, by eliciting the Maximal Individual Prototypic Facial Expressions along the circumplex dimensions of 16 psycho-physiological states. More specifically, the patient was asked to maximally pose with and without modal microscenarios (and with and without cognitive enhancement including mirror and guiding instructions) the maximal facial expressions for the following psycho-physiological states: disgust, anger, fear, tension, surprise, interest, joy/happiness, pleasure, love, friendly, content, calm, fatigue, boredom, sadness, and pain/suffering.

For each of 8 selected expressive psycho-physiological states, the photographs of four Maximal Individual Prototypic Facial Expressions were selected together with the patient to best fit the FEAMs and corresponding muscular activation patterns that commonly occur during the corresponding prototypic facial expressions for the relevant psycho-physiological states. After examining these expressions, the patient pointed out that she was most bothered by the unpleasant overexpression of the features displayed during the facial expressions of fear, but was also bothered by her features during facial expressions of anger, fatigue, and boredom. In general she stated that she wanted, if possible, a shift from more "negative" and "unpleasant" facial expressions to more "positive" and "pleasant" facial expressions.

Visual and tactile examination of the specific locations and activation intensities for the expressed facial features (FEAMs) and muscles during the elicitation of the Maximal Individual Prototypic Facial Expressions was done selectively along multiple dimensions, and the key findings were explained to the patient as necessary. Multidimensional evaluations of facial expressions done together with the patient revealed that her ideal balance of aesthetic and mimetic goals would involve BT targeting of selective features characteristic of the Maximal Individual Prototypic Facial Expression of "fear." These considerations guided the BT injections of specific muscles (Table 1, FIG. 1), with an understanding that overlapping facial features of other negative facial expressions including "anger," "fatigue" and "boredom" would also be diminished.

BOTOX® (onabotulinumtoxinA), available from Allergan, with global headquarters in Ireland) (referred to hereinafter as "BT" or "BOTOX®"), was injected to selectively decrease key components of the muscle activity characteristic of the "fear" facial expression by using previously published injection locations for relevant individual muscles and relatively lower doses than usually used for aesthetic treatments to preserve acceptable mimetic differentiation. It should be noted that BOTOX® from Allergan is provided by the manufacturer in units. In the upper face, the BT (dilution 4 units BT per 0.1 mL saline) injections were: 2 units (u) in the procerus, 4 u per side in the medial corrugator above the medial brow (above the inner canthus), and 2 u per side in the lateral corrugator in the corrugator depression ~1 cm above the superior orbital rim. Muscles were also injected in the upper forehead with 2 units/side in the medial frontalis, another 2 units/side more lateral and superior on the forehead to target the uppermost transverse lines produced by the frontalis, and 1 unit/side targeting the lateral frontalis.

Platysma and Risorius are commonly observed to work together in fear to stretch the mouth inferiorly and horizontally, so two BT injections (1 unit per injection, 2 injections per side) were injected into the platysma along the mandibular margin, lateral to the depressor anguli oris (DAO) based on palpation and known anatomy. The treatment also took into consideration the mild melomental asymmetry with downturned corners of the mouth being more pronounced on the right (particularly hyperexpressed during the expression of fear), and an additional 0.8 u of BT was injected in the playsma more laterally on the right side.

The patient was asked to precisely mimic (without a mirror) three times each of the quadruplicate Maximal Individual Facial Expressions for the 8 selected psycho physiological states (plus the baseline facial expression) before and 3 weeks after the BT injections. Triplicate mimicking facial expressions of each Maximal Individual Facial Expression were recorded, and the best corresponding mimicking expressions before and after procedure were chosen to be selectively and functionally compared in terms of intensity activation patterns for FEAMs and corresponding muscles. The same photographs were also shown to 3 observers to evaluate (in increments of about 10% in the degree of corresponding facial expression) the relative perceptive "signal value" along the dimensions of 8 psycho-physiological states and compared to the baseline (0%) and each corresponding Maximal Individual Prototypic Facial Expression (100%). The positive shifts and average perceptual values for mimicked facial expressions along 8 psycho physiological dimensions before and after BT are presented in FIG. 4.

The patient was extremely satisfied with the results of the multidimensional analysis and modulation of her facial expressions (FIG. 4). There was a perceived decrease in the expression of multiple facial displays characteristic of "negative" facial expressions (FIG. 4), mostly due to functional overlap (Table 1; FIG. 1) in the facial activation patterns of fear and other negative facial expressions.

According to the functional interactions within the Facial Expression Circumplex, LPS was not targeted even though it is a component of the fear prototype, to avoid the possibility of increasing the facial expression of somnolence/fatigue and decreasing the expressions of surprise, interest and awe (FIG. 1). The melomental depression under the corner of the mouth that is deepened obliquely (inferiorlaterally) by the platysma and risorious during fear, and downwards by DAO during sadness, could be further treated easily with hyaluronic acid fillers and BT as previously described in the literature; however, the patient was very satisfied with the improvement in her appearance during multidimensional evaluations after BT and felt no need for any further enhancements of her facial expressions. The average perceived "pleasantness" values relative to baseline facial expression (0%) by 3 observers for mimicked facial expressions along 8 dimensions (20% increments in the degree of expression) revealed a shift to less negative values for the "unpleasant" facial expressions after BT including fatigue (−25%->-3.3%), boredom (−48.3%->-5%), anger (−76.7%->-38.3%), and fear (−55%->-31.7%), while leaving the pleasant/unpleasant balance of the other expressions grossly unchanged including surprise (−10%->-5%), happy (88.3%->86.7%), friendly (63.3%->63.3%), and content (30%->26.7%).

The case illustrates for the first time the use of a multidimensional method to functionally analyze, measure, target, modulate, enhance and/or optimize selectively the key components of the individual prototypic facial expression patterns and perceptual spaces characteristic of whole facial expressions associated with basic expressive psychophysiological states.

EXAMPLE 2

Exemplary Step-by-Step Process

The following is a non-limiting illustration of an exemplary step by step process to measure, modulate, and optimize prototypic facial expressions and associated perceptual processes in terms of activation intensity patterns of FEAMs and muscles:

(1) Collection of photographic or video baseline (resting) and apex (maximal) facial expressions (elicited, mimicked, posed, spontaneous, felt or unfelt) providing a wide range of personal, functional and meaningful facial movements characteristic of basic expressive psycho-physiological states.

(2) The facial expressions from Step 1 judged to be most similar to the activated prototypic facial displays of psycho-physiological states are selected together with the patient to obtain functionally and personally relevant Maximal Individual Prototypic Facial Expressions. FIG. 1 helps in checking, selecting and establishing Individual Prototypic Facial Expressions of psycho-physiological states based on characteristic activations of muscles and corresponding FEAMs observed to occur during specific facial expressions of psycho-physiological states.

(3) Organization of the Maximal Individual Prototypic Facial Expressions around a Maximal Individual Facial Expression Circumplex of facial displays characterizing psycho-physiological states, therefore establishing a functional and meaningful maximal personal range of facial activation that can, in certain embodiments, be reproduced in a reliable manner through elicitation or mimicking before and/or after any procedures used to modulate facial expressions.

(4) Analysis of the patterns of whole (or selected parts) of facial expressions in the Maximal Individual Facial Expression Circumplex by measuring and reporting relevant personal activation intensity patterns of FEAMs and corresponding muscles that occur and co-occur during Maximal Individual Prototypic Facial Expressions for each psycho-physiological state.

(5) Review of the functional goals (aesthetic, mimetic differentiation, associated processes) for the different Maximal Individual Prototypic Facial Expressions of psycho-physiological states of interest with the patient or subject.

(6) Patients are asked to mimic (or in certain embodiments elicit) the relevant facial expressions of interest in the Maximal Individual Facial Expression Circumplex "before" and "after" the procedure is used to modulate facial expressions.

(7) Record the facial displays before the facial modulating procedure to obtain the "Pre-modulated" Facial Expressions of Psycho-physiological States by mimicking (or in certain embodiments eliciting) the Maximal Individual Prototypic Facial Expressions to obtain reproducible personal differentiation along the psycho-physiological dimensions of the "Pre-modulated" Facial Expression Circumplex.

(8) Analysis of the patterns of whole (or selected parts) of facial expressions in the Pre-modulated Facial Expression Circumplex by measuring and reporting the personal activation intensity patterns of FEAMs and corresponding muscles.

(9) Selective targeting of relevant facial features (balance points) based on the expressed components of Individual Maximal Prototypic Facial Expressions of psycho-physiological states in terms of measured and ideal intensity activation patterns of FEAM(s) and corresponding muscles.

(10) Optimization of modulation targets (intensity activations of FEAMs and corresponding muscles) by examining within the Maximal Individual Facial Expression Circumplex the functional interactions, limits and/or consequences of modulating selected FEAMs and corresponding muscles with approaches able to change facial aesthetic and mimetic function (animation) of faces, e.g., cosmetic, surgical, reconstructive or medical approaches.

(11) Individualizing the degree (e.g., adjust the BOTOX® doses) and manner (e.g., establish the optimal activation intensity of specific individual FEAMs that will guide the specific sites of treatment with hyaluronic acid) of intervention with modulating approaches to enhance faces in a predictable manner meant to integrate the objective optimization of functional target goals (desired aesthetic, mimetic differentiation goals and associated processes) of individual patients.

(12) Record the facial displays after the facial modulating procedure(s) to obtain the Modulated Facial Expressions of Psycho-physiological States, by mimicking (or in certain embodiments eliciting) the facial expressions organized along the Maximal Individual Facial Expression dimensions of psycho-physiological states to obtain reproducible novel personal differentiation along the Modulated Facial Expression Circumplex.

(13) Following perceptual evaluation of the recorded facial expressions by observers along multiple dimensions (categories) of psycho-physiological states, functional multi-dimensional analysis of the reported perceived mimetic differentiation and aesthetic "signal values" of the "pre-modulated" and "modulated" facial expressions is done by establishing the dimensional coordinates in perceptual judgment spaces and resulting shifts, taking the following embodiments in the current invention:

(i) after establishing the baseline facial expression as 0% perceptual "signal value" and each recorded Maximal Individual Prototypic Facial Expression of selected psycho-physiological states as being 100% (the radius for the corresponding state in the circumplex circle), relative dimensional shifts in measured perceived basic emotions and other psycho-physiological states for the newly modulated facial expressions are visualized as deviations from this circle along the corresponding multiple dimensional states of the Facial Expression Circumplex ("spider" or "radar-type" graphs can be used to visualize the results); and (ii) measuring the perceptual "signal value" coordinates of the newly obtained facial expressions along bipolar dimensional continuums using an 11 point scale (−5 to +5 or −100%, −80%, −60%, −40%, −20%, 0, +20%, +40%, +60%, +80%, +100%, with 0% being the baseline facial expression and (+/−)100% being internal maximum standards along the bipolar continuums) including for, but not limited to, the following perceptual dimensions:

(a) functional mimetic dimension axis signals: x-axis (pleasure, displeasure); y-axis (unresponsiveness, arousal);

(b) functional bi-polar mimetic dimension signals: lethargic, alert; apathic, surprised; tired, energized; fatigue, awe; bored, interested; resigned, hopeful; shame, pride; insecure, confident; miserable, elated joy; sad, happy; pain, comfort; suffering, ecstasy; displeasure, pleasure; disgust, love; contempt, respect; upset, satisfied; angry, friendly; rage, amusement; hostile, peaceful; fear, serene (content); agitated (anxious), calm; tense, relaxed; unresponsive, aroused;

(c) functional mimetic aesthetic signals: pleasantness; perceived relative age (relative to specified time range); etc.

(14) Compare the facial expressions, muscles and FEAMs measurements of psycho-physiological states from the Pre-modulated Facial Expression Circumplex with the corresponding facial expressions and measurements from the Modulated Facial Expression Circumplex to review and optimize the results of the facial modulating approach, as well as to further refine and balance any new functional goals (aesthetic, mimetic differentiation of facial expressions, associated processes and perceptual spaces) with the patient or subject.

In further embodiments of the technology, other applications or individual steps may be present:

(15) Compare psychological (behavioral, intention, communicative, etc) and FEAMs (and corresponding muscles) measurements from the Pre-modulated Facial Expression Circumplex with the corresponding measurements from the Modulated Facial Expression Circumplex to determine the optimal psychological correlates for selective lesional models of facial expressions based on targeting the individual prototypic facial expression component(s) of basic emotions and psycho-physiological states.

(16) Compare psycho-pathological (including but not limited to phobias, posttraumatic stress syndrome, anxiety disorders, performance anxiety, public speech anxiety, anorexia, addiction disorders, etc.) and FEAMs (and corresponding muscles) measurements from the Pre-modulated Facial Expression Circumplex with the corresponding measurements from the Modulated Facial Expression Circumplex to determine the optimal psycho-pathological correlates for selective lesional models of facial expressions based on targeting individual prototypic facial expression component(s) of basic emotions and psycho-physiological states.

In conclusion, the combination of selective quantitative measurements, analysis, modulation and optimization of the activation intensities of FEAMs and corresponding muscles to characterize and elicit the optimal Individual Prototypes of Facial Expression, combined with determinations of the perceptual signal values of newly modulated faces along multiple coordinates of psycho-physiological dimensions, provide a strong and unique foundation that allows the current technology to properly balance and optimize facial expressions and associated perceptual processes in a safer, more comprehensive, reliable, reproducible, and efficient way than previously possible.

All embodiments described herein are illustrative and in no way limit the scope of the technology and the technology may be embodied in other forms not explicitly described here, without departing from the spirit thereof.

Figure 5:
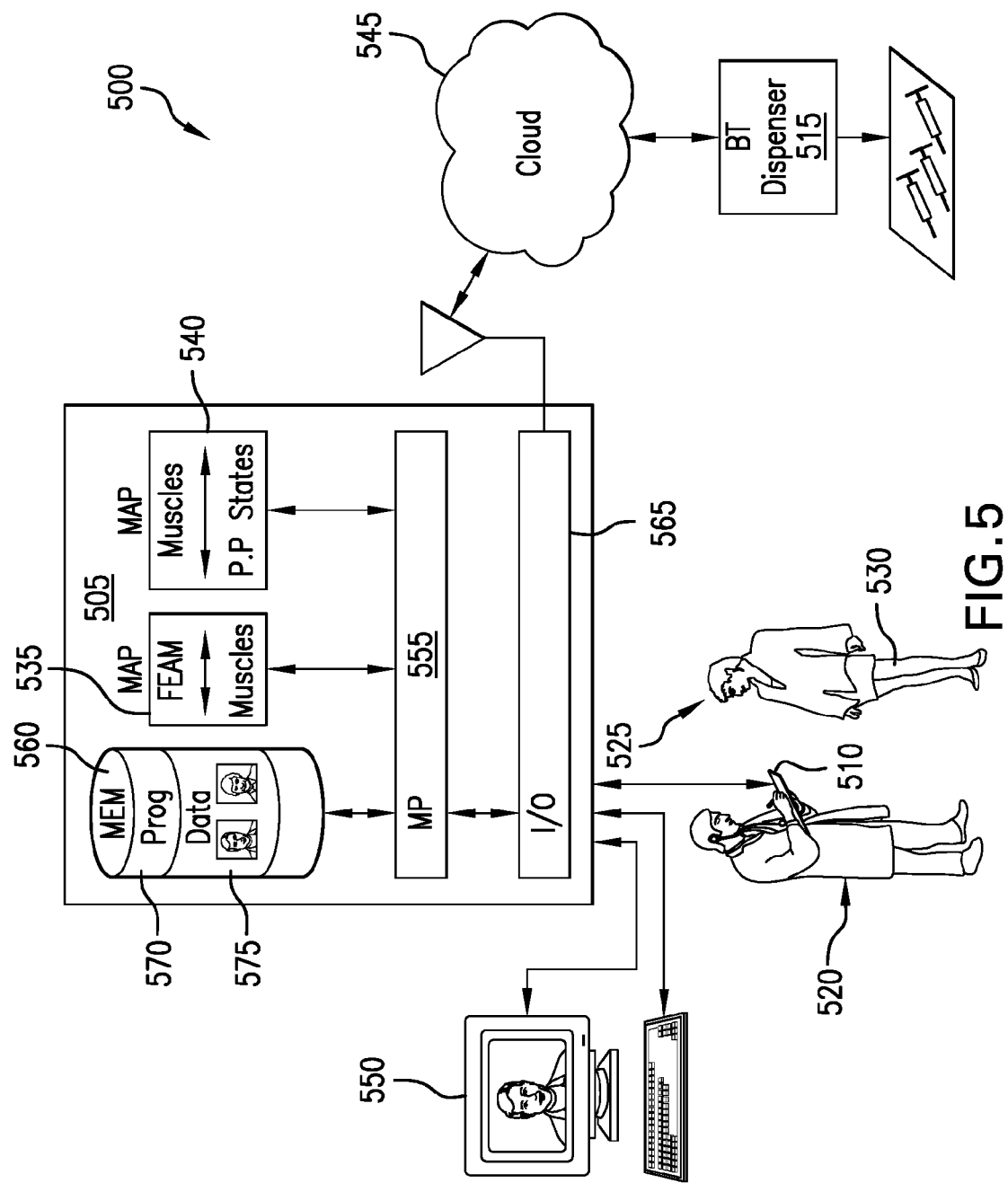

FIG. 5 illustrates a block diagram of an exemplary botulinum toxin (BT) treatment system. In FIG. 5, an exemplary BT treatment system 500 includes a computer 505, a camera 510 and a BT dosimeter 515. The computer is depicted having a microprocessor 555 coupled to memory 560 and input/output circuitry 565. The memory 560 is depicted having program memory locations 570 and data memory locations 575. A physician 520 is using the camera 510 and photographing a face 525 of a patient 530. One or more facial images may be captured by the camera 510 and transferred to the computer 505. In some embodiments, various facial expressions of psycho-physiological states may be induced in the patient 530. Each facial image captured by the camera 510 may be associated with a particular psycho-physiological state, for example. In some embodiments, many images may be captured, each associated with a psycho-physiological state. In some embodiments, an image may be taken with the patient assuming a relaxed state, wherein facial muscular activation may be low.

After facial images have been collected, each of which being associated with a psycho-physiological state, the patient and doctor may preview the images. In some embodiments, the patient and doctor may select from among the images a subset to use in the generation of a treatment program. After selecting images to be used in determining a BT treatment plan, the doctor and patient may identify one or more FEAMs that are considered to be a candidate for modification. In some embodiments, the selection of FEAM modification candidates may be performed by selecting an image for display on a display device 550. A selection cursor may be positioned above the display device to select the FEAM modification candidate.

After one or more FEAMs have been selected as candidates for modification, the muscles that control such FEAMs may be determined, and a determination may be made whether to target the FEAMs with muscle modulating procedures like BT or in combination with other agents and procedures that would alter only the skin surface and texture FEAMs (S, E, D, I) without significantly affecting the FEAMs characterizing distances (R, C). In some embodiments, a mapping 535 between the FEAM and the muscle or muscles that create such a FEAM may be used to create a list of muscles candidates for treatment. Each muscle or muscle group that controls a particular FEAM may also control a related FEAM elicited by the same or a different psycho-physiological state. In an exemplary embodiment, a mapping 540 between the muscle or muscle groups and the FEAMs that are controlled by such muscles may be employed. For example, if selected FEAM is from an image that was elicited with an expression of fear, the same muscle or muscles that create the selected FEAM may also create a related FEAM elicited with an expression of excitement. A patient may desire to reduce the intensity of the FEAM for the expression of fear, but may also have no desire to reduce the related FEAM for the expression of excitement. These two competing desires must be weighed and reconciled in the determination of treatment.

In some embodiments, after the one or more FEAMs have been selected and the FEAM creating muscles identified, the images corresponding the related FEAMS may be presented to the patient and doctor. As each image is displayed, for example, the patient and doctor may assign a weight corresponding to the amount of FEAM modification desired for that psycho-physiological state's expression. A single muscle of muscle group may have one or more weights assigned to it, each one corresponding to one of the related FEAMs. In some embodiments, a treatment dose may be determined using an average of the various assigned weighting values. In some embodiments, each of the selected images may be sequentially presented. As each image is presented, the FEAMs related to previously selected FEAMs may be annotated. The patient and doctor may select new FEAMs as well as assigning weights for modification of the annotated related FEAMs.

After all of the selected images have been presented, and all of the FEAMs candidates and related FEAMs have been assigned weights for all of the images, a treatment plan may be determined. In some embodiments, the images may have to be cycled through more than one time to ensure that all related FEAMs have been presented to be assigned a weight. In an exemplary embodiment, after the treatment program has been determined, the treatment plan may be presented in various manners. For example, an image may be displayed with treatment locations annotated. In some embodiments, an associated dosage annotation may be presented for each treatment location. In some embodiments, the treatment plan may be transmitted to an automated dosimeter for preparing the syringes for actual treatment. In the figure, the transmission of the treatment plan may be via a cloud 545 or wire-less network, for example.

Figure 6:
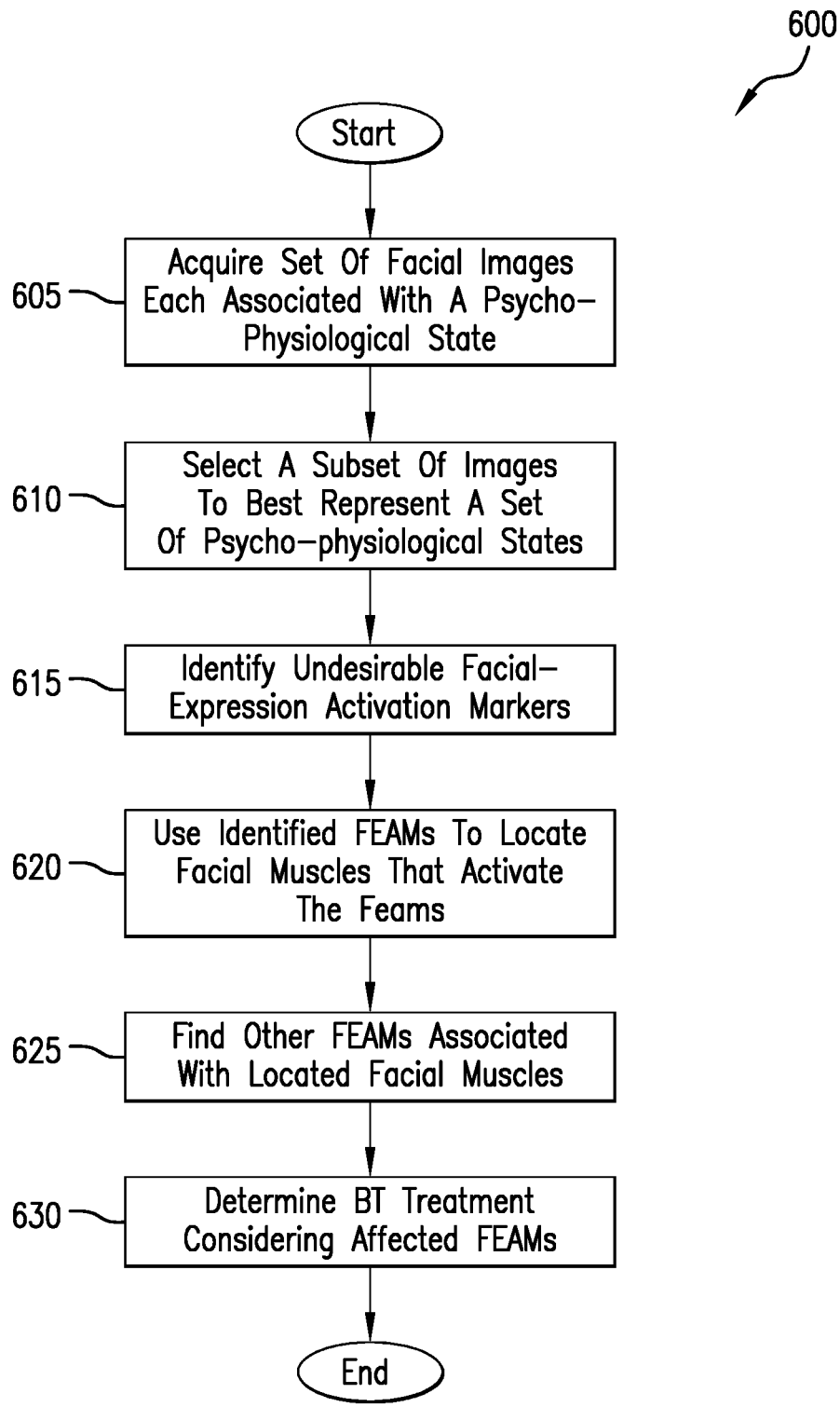

FIG. 6 depicts an exemplary top-level method for determining a BT treatment plan. In the FIG. 6 embodiment, a flow chart 600 of treatment method is detailed from the vantage point of an observer of the method. First, a set of facial images is acquired, each of which is associated with a specific psycho-physiological state 605. Then, a subset of the acquired images is selected to best represent a set of the psycho-physiological states 610. Then undesirable facial expression activation markers (FEAMs) are identified in the selected images 615. Then the identified undesirable FEAMs are used to locate facial muscles that activate the undesirable FEAMs 620. In some embodiments, a map associates the FEAMs of various psycho-physiological states with muscles in the face and neck, for example. After the muscles are located, they are used to find other FEAMs associated with the located facial muscles 625. In some embodiments, a mapping between each facial muscle and a FEAM may be used in step 625. Finally, a treatment program is determined, the determination includes considerations of all FEAMs affected by each muscled proposed to be treated 630. In some embodiments, the treatment program may include a file containing all treatment sites and dosages of BT alone or in combination with other agents and procedures able to modulate FEAMs. In an exemplary embodiment, the treatment program may include an image annotated with pertinent treatment information.

Figure 7:
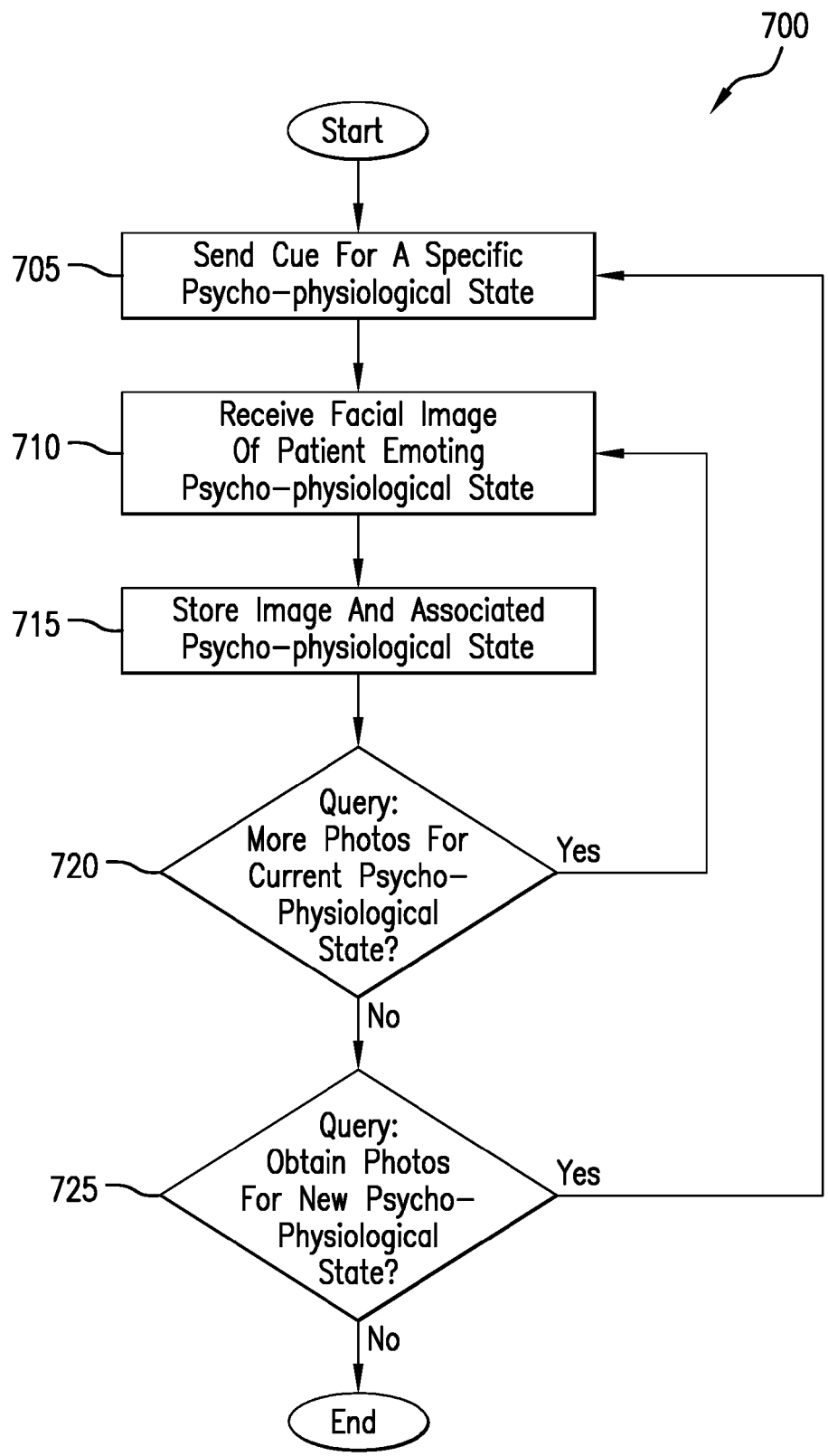

FIG. 7 depicts a flow-chart of an exemplary method of acquiring a set of facial images. In the FIG. 7 embodiment, an exemplary image acquisition step 605 will be described from the vantage point of the processor 555 of the exemplary BT treatment system 500. An exemplary image acquisition method 700 begins by the processor sending a cue for a specific psycho-physiological state 705. In an illustrative embodiment, the processor 555 may send an image file for display on a display device, the image file depicting an exemplary psycho-physiological state. For example, if the psycho-physiological state is fear, then the processor 555 may send an image of a person's face displaying a response of fear. In some embodiments, the processor 555 may simply send a message or an eliciting micro-scenario to the display device indicating the desired psycho-physiological state. After sending the cue, the processor 555 receives the facial image of the patient emoting the cued psycho-physiological state 710. Then the processor stores the received image and associates it with the elicited response to the cued psycho-physiological state 715. The processor then queries the user as to whether more photos for the current psycho-physiological state are needed 720. If the processor 555 receives a response from the user that more photos are needed, the processor 555 returns to step 710. If, however, the processor 555 receives a response from the user, that not more photos are needed, then the processor 555 queries the user as to whether to obtain more photos of the patient corresponding to other psycho-physiological states 725. If the processor 555 receives a response from the user that images for other psycho-physiological states must be obtained, the processor 555 returns to step 710. If, however, the processor 555 receives a response from the user indicating that no other images need to be obtained, the method ends.

Figure 8:
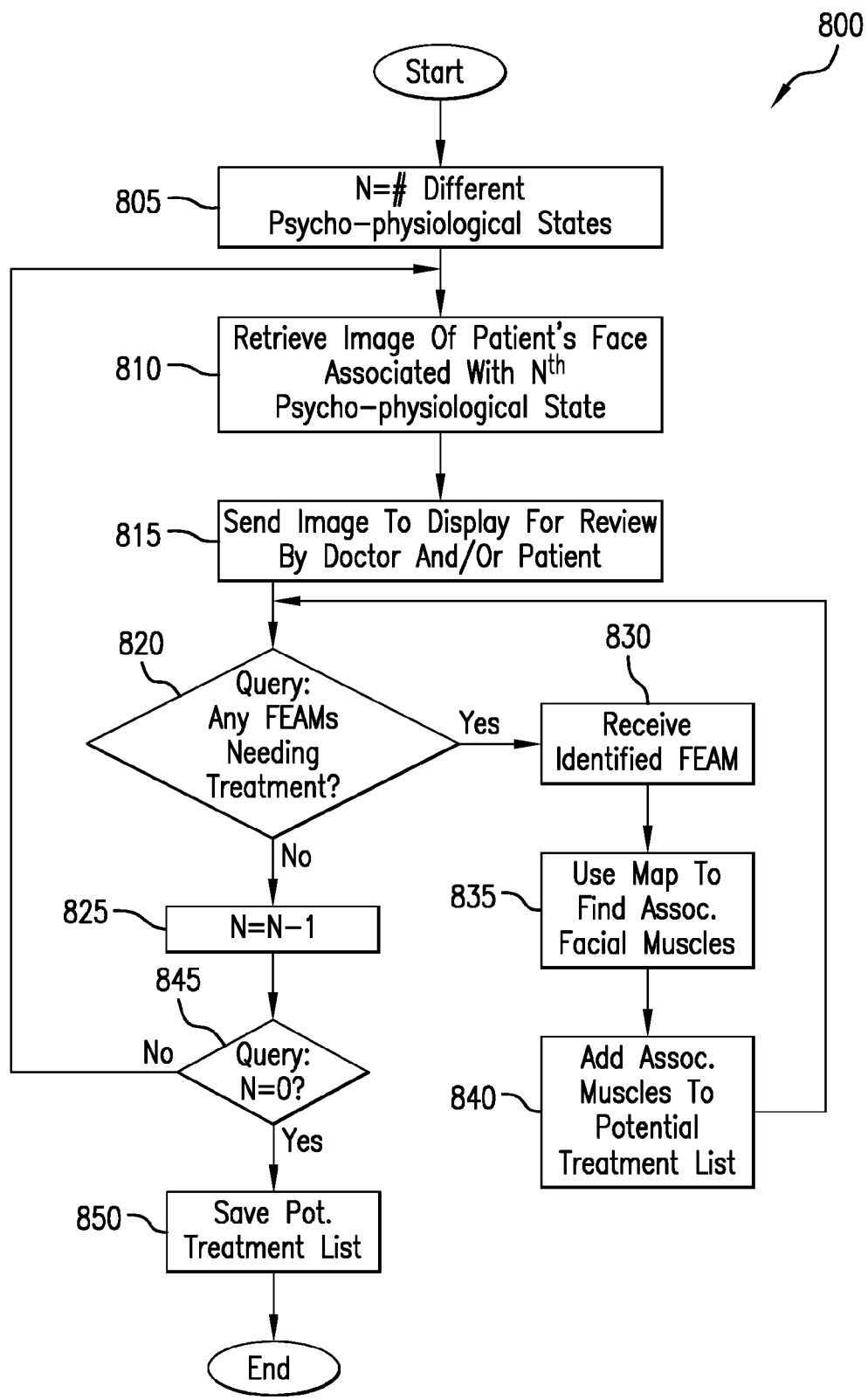

FIG. 8 depicts an exemplary method of identifying undesirable facial-expression activation markers. In the FIG. 8 embodiment, an exemplary FEAM identification step 615 will be described from the vantage point of the processor 555 of the exemplary BT treatment system 500. An exemplary undesirable FEAM identification method 800 begins by the processor 555 setting the number N of different psycho-physiological states 805. Then the processor 555 retrieves an image of the patient's face associated with the Nth psycho-physiological state 810. Then the processor 555 sends the retrieved image to the display for review by the doctor and/or patient 815. The processor 555 then queries the user as to whether any FEAMs displayed in the image require treatment 820. If the processor 555 receives a response from the user indicating that a displayed FEAM requires treatment, the processor 555 then receives an identified FEAM 830. In some embodiments the FEAM may be identified using a mouse. In some embodiments, the doctor may indicate the technical name of the FEAM. The processor 555 then uses a mapping to find the muscle or muscles that are associated with generating the identified FEAM 835. Then the processor 555 will add the associated FEAMs and corresponding muscle or muscles to a list of potential treatment of muscles and FEAMs/locations. Then the processor 555 will return to step 820. If back at step 820, the processor 555 receives a response from the user that no depicted FEAMS required treatment, the processor decrements the counter N of the number of remaining psycho-physiological states for review 825. Then the processor 555 tests whether the number of remaining states is equal to zero. If the number of remaining states is not equal to zero, the processor 555 returns to step 810. If, however, the number of remaining states in zero, the processor 555 saves the list of potential treatment of muscles and FEAMs/locations 850. Then the method ends.

Figure 9:
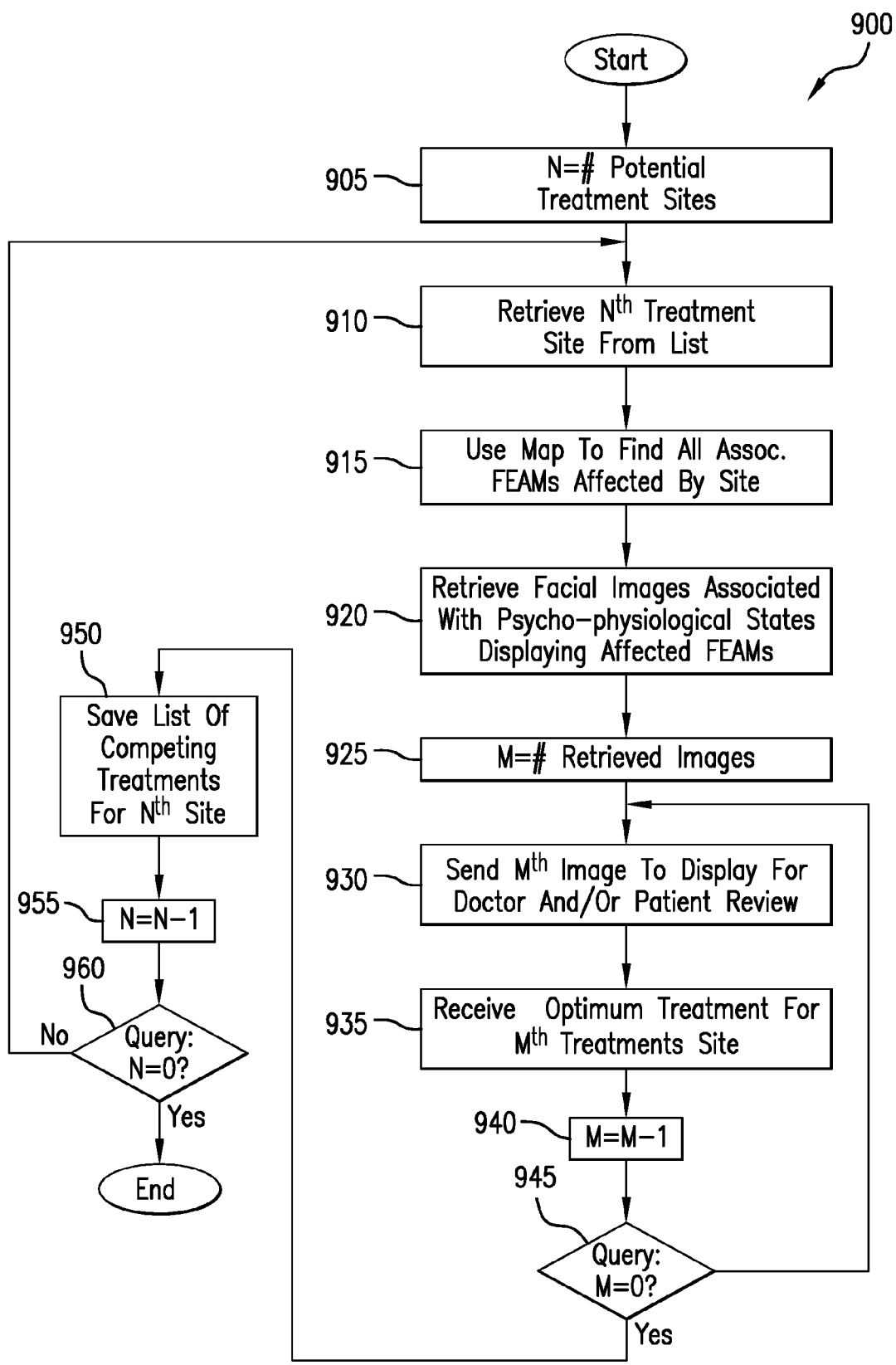

FIG. 9 depicts an exemplary method of finding FEAMS associated with specific muscles or muscle groups. In the FIG. 9 embodiment, an exemplary FEAM association step 625 will be described from the vantage point of the processor 555 of the exemplary BT treatment system 500. An exemplary associated FEAM finding method 900 begins by the processor 555 setting the number of potential treatment sites 905. For example, this number of potential treatment sites may calculated by counting the number N of potential treatment muscles and FEAMs/locations generated in the FEAM identification method 800. The processor 555 then retrieves the Nth treatment muscle/location from the list 910. The processor 555 then uses a map to find all associated FEAMs affected by the retrieved muscle/location 915. Then the processor 555 retrieves the facial images associated with the psycho-physiological states that display the affected FEAMs 920. The processor 555 then counts the number M of retrieved images 925. The processor 555 then sends the Mth retrieved image to the display device for review by the physician and/or patient 930. Then the processor 555 receives, from the user, an optimum treatment plan for this Mth treatment site 935. The processor 555 then decrements the associated image counter M 940. The processor 555 then tests whether any remaining associated images need review by testing if M is zero 945. If M is not equal to zero, the processor 555 returns to step 930. If, however, M does equal zero, the processor 555 saves the list of competing treatments associated with the Nth treatment site 950. The processor 555 then decrements the treatment site counter N 955. The processor 555 then tests whether any remaining treatment sites require processing by testing if N equals zero 960. If M is not equal to zero, the processor 555 returns to step 910. If, however, M does equal zero, the method terminates.

Figure 10:
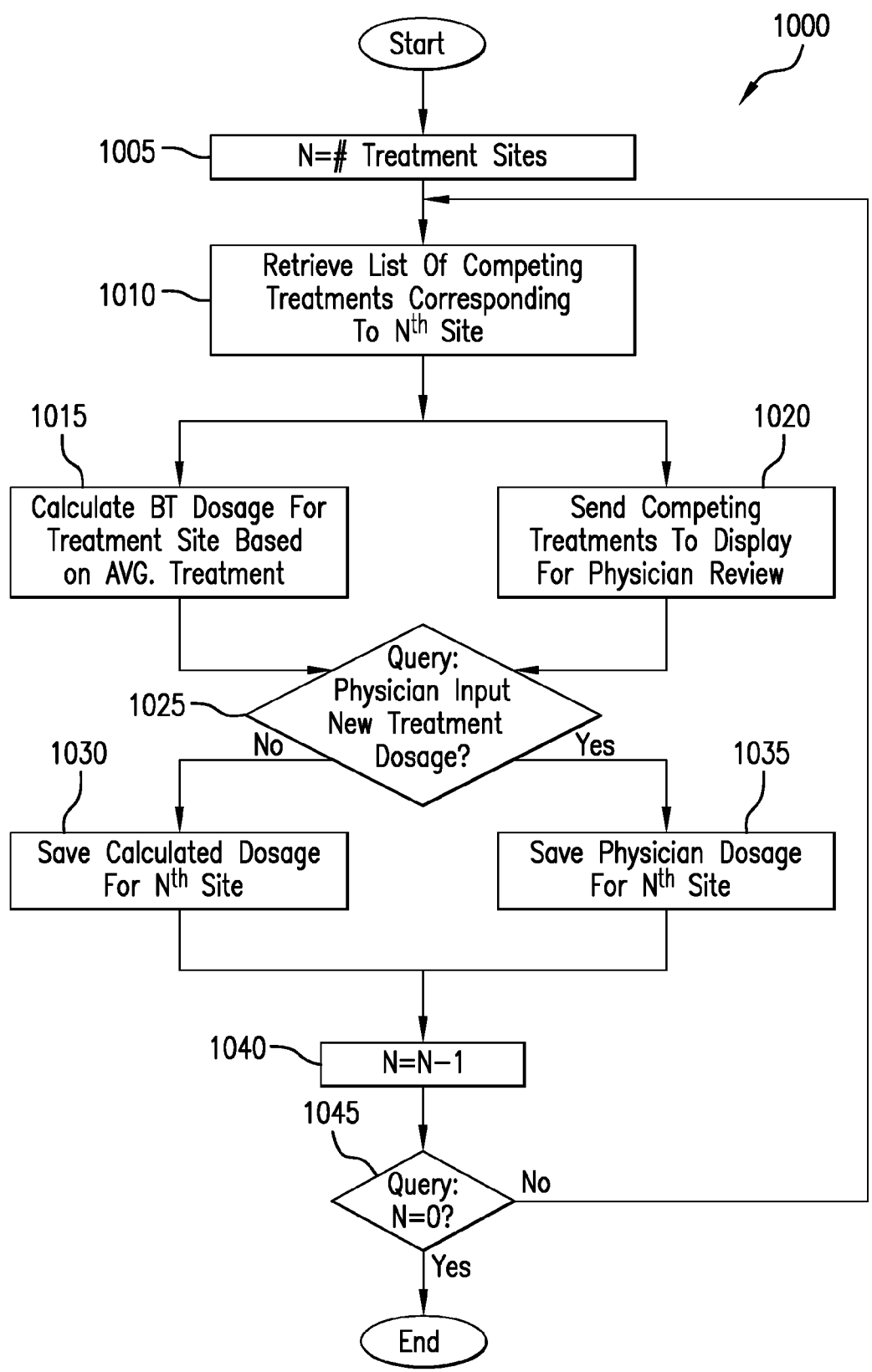

FIG. 10 depicts an exemplary method for determining a treatment plan while considering competing treatments for all treatment sites. In the FIG. 10 embodiment, an exemplary treatment determination step 630 will be described from the vantage point of the processor 555 of the exemplary BT treatment system 500. An exemplary treatment determination method 1000 begins by the processor 555 setting the number of proposed treatment sites 1005. For example, this number of proposed treatment sites may calculated by counting the number N of potential treatment muscles/locations generated in the FEAM identification method 800. The processor 555 then retrieves a list of competing treatments corresponding to the Nth treatment site 1010. For example, this list may be one generated in the step 950 of the associated FEAM finding method 900. Next, the processor 555 calculates a BT dosage using all the information of the retrieved list 1015. In some embodiments, the list may include a dosage associated with each competing or conflicting FEAM. In some embodiments, the list may include a weight assigned to the importance of the dose associated with the FEAM entry. In some embodiments, the processor 555 may perform a weighted average or another assigned calculation of the dosages in the list using the associated weighting values. The processor 555 also sends the competing or conflicting treatment information to the display for review by the physician 1020. The processor then queries the user asking if the physician wishes to use the calculated dosage or if the physician desires to provide a different dosage or another type of treatment able to modify a FEAM 1025. If the processor 555 receives a response indicating that the physician provided a different dose, the processor 555 saves the physician supplied dosage for this Nth treatment location 1035. If, however, the processor 555 receives a response indicating that the physician wants to use the calculated dosage, then the processor saves the calculated dosage associated with the Nth treatment site 1030. Regardless of which dosage is saved, the processor 555 then decrements the treatment site counter N 1040. The processor 555 then tests if more treatment sites need consideration by testing if N equals zero 1045. If N does not equal zero, the processor 555 returns to step 1010. If, however, N does equal zero, then the method terminates.

Figure 11:
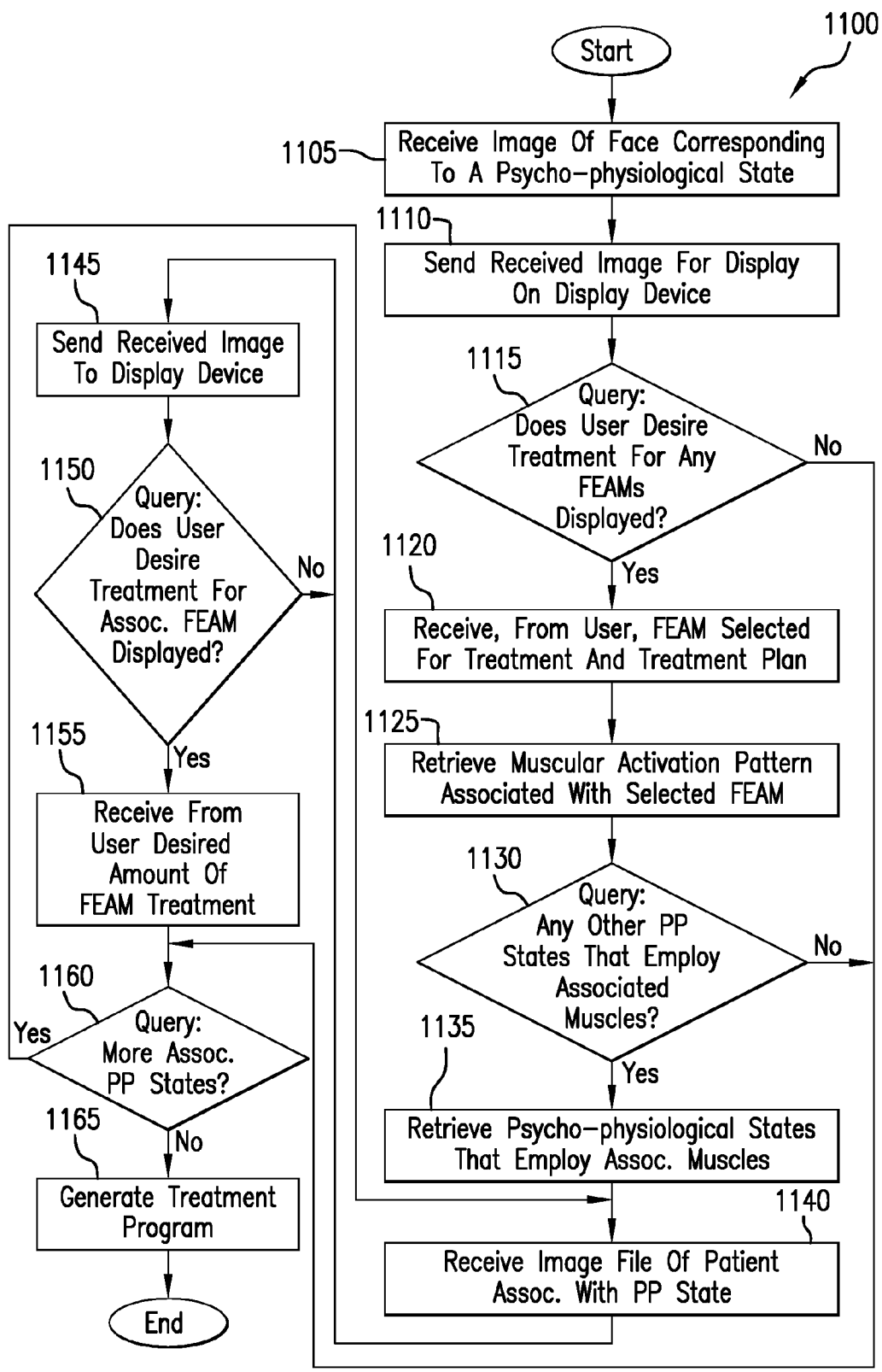

FIG. 11 depicts an exemplary method used in an exemplary BT treatment computer program. In the FIG. 11 embodiment, a BT treatment method 1100 begins by the processor 555 receiving a file containing an image of a face corresponding to a psycho-physiological state 1105. The processor 555 then sends the received image for display on a display device 1110. The processor 555 next queries the user as to if the user desires treatment for any of the FEAMs displayed in the image 1115. If the processor 555 receives a response from the user indicating that the user does desire to treat one or more of the displayed FEAMs, the processor then receives, from the user, information indicative of which FEAM the user selects 1120. The processor then retrieves the muscular activation pattern associated with the selected FEAM 1125. The processor 555 then tests if the muscles associated with the muscular activation pattern affect any other FEAMs displayed in images associated with other psycho-physiological states 1130. If other FEAMs are affected by the muscles associated with the muscular activation pattern, the processor 555 retrieves the psycho-physiological states that employ the associated muscles and FEAMs 1135. The processor 555 then receives image files of the patient associated with the retrieved psycho-physiological states 1140. Next, the processor 555 sends the received image file to the display for review by the patient and/or doctor 1145. The processor 555 then queries the user as to the user's desired treatment for the associated FEAM displayed 1150. If the processor 555 receives a response from the user indicating that the user does desire to treat the associated FEAM, the processor 555 receives from the user the desired treatment information 1155. The processor 555 then tests whether more psycho-physiological states are associated with the muscles under consideration 1160. If more psycho-physiological states are associated with the muscles under consideration, then the processor 555 returns to step 1140. If, however, no more psycho-physiological states are associated with the muscles under consideration, then the processor 555 generates a treatment program 1165, and then terminates the method. If back at step 1115 the processor 555 receives a response from the user that no treatment is desired for the displayed image, then the processor 555 advances to step 1160. The processor 555 also advances to step 1160 if at step 1130 the processor 555 determines that no other psycho-physiological states employ the associated muscles and FEAMs. The processor 555 also advances to step 1160 if at step 1150 the processor 555 receives a response from the user indicating that the user doesn't desire to treat the associated FEAM.

For more than 200 years, studies have gradually revealed the main components of facial expressions and their muscular basis (Hjortsjo, 1970). These studies culminated with the development of the "Facial Action Coding System" (FACS) by Ekman and Friesen in the 1970s. FACS is a method of analyzing and measuring facial expressions in terms of intensity patterns of facial "Action Units" (AUs) derived from the actions of one or more muscles. The FACS has been used in psychology, neuroscience, artificial intelligence, criminal law and medicine.

Nevertheless, progress has been slow in understanding the personal functional, perceptual and communication effects and implications of facial modulation by modern aesthetic and reconstructive approaches on perceived functional "signal value" (aesthetic, mimetic, and associated processes) during the expression and transmission of whole facial gestalts or individual components. These effects are particularly poorly characterized, studied and understood in the whole face, in great measure due to a lack of sufficiently detailed functional anatomic methods that are able to properly measure and approach the complexity and components of individual human facial expression in sufficient detail.

For many people, facial wrinkles and unsightly facial expressions often occur due to overactivity of the underlying facial musculature. While the current aesthetic approaches are mostly directed at decreasing the appearance of isolated facial features of aging such as wrinkles, facial expressions can also be modulated by surgical, reconstructive and medical aesthetic procedures just for the specific purpose of changing facial expressions and associated processes. This can be done by modulating the movement of facial tissue, changing the shapes and relative positions of topographic facial components, including expression lines. Most efforts to modulate human faces and their perceptions focus mostly on decreasing isolated unpleasant aesthetic features (such as localized hyperdynamic lines and wrinkles) in facial expressions at rest or during elicitation of simple muscle movements. These simple, isolated muscle movements are generally not fully meaningful on a personal and functional level, being not fully representative of the complex expressions characteristic of emotional states in the whole face. Due to the complexity of comprehensively analyzing interacting facial expression features and difficulty to reliably elicit them in a fully differentiated and functional fashion during the expression of various mental states, facial procedures and agents are often used for purely cosmetic or gross reconstructive purposes guided mostly by isolated or localized aesthetic considerations. This is often done without a more subtle comprehensive understanding of the important effects that modulating procedures can have on the function (aesthetic, mimetic, associated perceptual processes, signal communication, facial feedback, etc.) of full facial displays during the expressions of multiple basic emotions and other psychophysiological states.

To date, no efforts have been made to try to modulate facial expressions based on a more functional, multidimensional, comprehensive "full face" approach that takes into account the shared, interacting and differential components of facial prototypes expressed during various expressive psycho-physiological states. Furthermore, currently there is no functional method to selectively, reproducibly and systematically produce, measure, modulate or optimize the individual facial expressions and features that are characteristic of basic emotions and other expressive psycho-physiological states in a reliable and balanced manner, in a way that preserves acceptable mimetic facial differentiation and takes into consideration the complex differential interactions and activations of functional anatomic expression markers and muscles that occur as communication signals during different psycho-physiological states.

Facial expressions of psycho-physiological states can be adaptive or maladaptive, depending on personal circumstances, context and goals. For example, failure to display or recognize a differentiated facial expression of fear in combat has different adaptive value (and very different consequences) than overexpressing fear during posttraumatic shock syndrome or phobias in social contexts such as conversation or speech. The optimization of facial expressions is complex also because depending on context and individual, a simple facial movement like, e.g., eyebrows raising caused by the frontalis muscle can communicate or be a part of various facial expressions of psycho-physiological states. Similarly, depending on natural and artificially-induced individual variations in functional anatomy, tissue characteristics and neuromotor supply, the mentalis muscle can produce different facial movements (raise the chin and protrude the lip) and topographic appearance changes in the shape and form of facial features (for example, chin wrinkles, dimples, and lip contour), that can then be expressed in many individuals during the psychophysiological states of sadness, anger, disdain, and doubt.

Alteration and complete effacement of facial markers (FEAMs) by modern approaches such as ablations (laser, nerve, etc.), chemical peels, botulinum toxin and other medical approaches have the potential to interfere with both inter- and intra-personal communication of human facial expression signals. These can at times produce unintended and undesirable long-term consequences (e.g., an artificial permanent "look of surprise" or the impression of a "paralyzed" face). Thus, the right personal balance of functional goals (mimetic differentiation, signal communication, aesthetic, facial feedback, etc.) should be clearly and (if possible) more quantitatively measured, specified, designed or modulated if one attempts to properly optimize and modulate facial expressions.

Currently practiced methods to assess, measure, produce, reproduce and modulate individual facial expressions have significant inherent and practical limitations in dealing with personal facial features that occur due to localized neuromotor and functional anatomic variations. The current methods also fail to encompass and predictably manage the functional complexity of the whole face characterizing facial expressions of basic psychophysiological states by not taking into account the differential intensity activation patterns of facial features and muscles that can also have significant interacting and overlapping components with other characteristic facial displays of different basic emotions and other expressive psycho-physiological states. Furthermore, there is a lack of functional testing methods able to determine the quantitative and qualitative perceptual effects that the newly modulated whole faces have on an observer's decoding judgments.

In certain embodiments, the present technology is directed to a method for achieving a desired facial expression on the face of a subject, the method comprising the steps of: (a) measuring the activation intensity or intensities of one or more facial expression activation markers (FEAMs) of the subject affecting a desired facial expression; (b) determining the activation intensity or intensities of one or more optimal FEAMs affecting the desired facial expression; (c) grouping the one or more optimal FEAMs into one or more functional sets, each set comprising a desired optimal pattern of FEAMs and each set corresponding to a muscle activity optimally approximating the desired expression; and (d) applying an agent or procedure to the face, head or neck of the subject to implement the desired optimal pattern of FEAMs and corresponding muscle activity for the desired facial expression.

In certain embodiments, the desired facial expression is indicative of a basic expressive psycho-physiological state chosen from worry, anxiety, fear, rage, anger, irritation, contempt, disgust, pain, despair, distress, sadness, shame, boredom, fatigue/somnolence, calmness, serenity, friendliness, amusement, relief, delight, pleasure, happiness, love, pride, elated joy, awe, interest, surprise, eyebrow flash greeting, novelty, expectation, goal attainment, power/control, external/internal standards disturbance, intrinsic pleasantness, or a combination of any of the foregoing.

In certain embodiments, the determination of the activation intensity or intensities of one or more optimal FEAMs affecting the desired facial expression in step (b) comprises analyzing and testing the interactions and effects of FEAM changes on functionally relevant full face expressions and associated perceptual spaces of two or more basic expressive psycho-physiological states.

In other embodiments, the present technology is directed to a method for modulating the expression of a psycho-physiological state in a subject, the method comprising the steps of: (a) measuring one or more facial expression activation markers (FEAMs) and corresponding muscle activity of the subject for the psycho-physiological state; (b) determining one or more optimal FEAMs and corresponding desired muscle activity of the subject for the psycho-physiological state; (c) relating the optimal FEAM to a desired muscle activity that triggers the FEAM; (d) identifying an agent and optimal dosage of the agent that modulates the desired FEAM and muscle activity; (e) identifying an optimal site on the body of the subject that modulates the desired FEAM and muscle activity when contacted with the agent; and (f) applying the optimal dosage of the agent to the body of the subject to implement the desired FEAM and muscle activity, wherein the implementation of the desired FEAM and muscle activity achieves the optimal modulation in the expression of the psycho-physiological state of the subject.

In other embodiments, the present technology is directed to a method for optimally modulating the expression of a psycho-physiological state in a subject, the method comprising the steps of: (a) eliciting and determining the individual patterns of facial expression markers (FEAMs) and corresponding muscle activity during the expression of a psycho-physiological state in a subject (the Maximal Individual Prototypical Facial Expression of the psycho-physiological state); (b) determining an optimal pattern of FEAMs and corresponding desired muscle activity of the subject for the psycho-physiological state; (c) relating the pattern of FEAMs to a desired muscle activity that triggers the optimal FEAM; (d) identifying an agent and optimal dosage of the agent that modulates the desired FEAM and muscle activity; (e) identifying an optimal site on the body of the subject that modulates the desired FEAM and muscle activity when contacted with the agent; and (f) applying the optimal dosage of the agent to the body of the subject to implement the desired FEAM and muscle activity, wherein the implementation of the desired FEAM and muscle activity achieves the optimal modulation in the expression of the psycho-physiological state of the subject.

In certain embodiments, the present technology is directed to a method for achieving a desired optimal facial expression on the face of a subject, the method comprising the steps of: (a) measuring one or more facial expression activation markers (FEAMs) of the subject affecting a desired facial expression; (b) determining one or more optimal FEAMs affecting a desired facial expression by analyzing the interactions and effects of optimal FEAMs on two or more functionally relevant facial expressions, e.g., on full facial expressions characteristic of basic emotions and other psycho-physiological states; (c) grouping the one or more optimal FEAMs into one or more functional sets, each set comprising a desired optimal pattern of FEAMs and each set corresponding to an optimal muscle activity characterizing the desired expression; and (d) applying an agent or procedure to the face, head or neck of the subject to implement the desired optimal pattern of FEAMs, corresponding muscle activities and perceptual signal values for the desired facial expression and associated expressions of functionally relevant psycho-physiological states.

In other embodiments, the present technology is directed to a method for modulating the expression of a psycho physiological state in a subject, the method comprising the steps of: (a) measuring one or more facial expression activation markers (FEAMs) and corresponding muscle activity of the subject for the psycho physiological state; (b) determining optimal pattern of FEAMs and corresponding desired muscle activity of the subject for the psycho physiological state; (c) relating the optimal FEAM to a desired muscle activity that triggers the FEAM; (d) identifying an agent and optimal dosage of the agent that modulates the desired FEAM and muscle activity; (e) identifying an optimal site on the body of the subject that modulates the desired FEAM and muscle activity when contacted with the agent; and (f) applying the optimal dosage of the agent to the body of the subject to implement the desired FEAM and muscle activity, wherein the implementation of the desired FEAM and muscle activity achieves the modulation in the expression of the psycho physiological state of the subject.

In other embodiments, the present technology is directed to a method for optimally modulating the expression of a psycho-physiological state in a subject, the method comprising the steps of: (a) eliciting and determining the individual patterns of facial expression markers (FEAMs) and corresponding muscle activity during the expression of a psycho-physiological state in a subject (the Maximal Individual Protypical Facial Expression of the psycho-physiological state); (b) relating the pattern of FEAMs to sets of corresponding muscle activity that can be targeted to affect and benefit the expression of the psycho-physiological state; (c) determining an optimal pattern of facial expression activation markers (FEAMs) and corresponding desired muscle activity to optimally modulate the expression of the psycho-physiological state; (d) identifying an optimal site on the body of the subject that modulates the desired FEAMs and muscle activity when contacted with the agent; (e) identifying an agent and optimal dosage of the agent that modulates the desired FEAMs, perceptual signal value and muscle activity to correspond to the optimal expression of the psycho-physiological state; and (f) applying the optimal dosage of the agent to the body of the subject to implement the desired FEAM and muscle activity, wherein the implementation of the desired FEAM and muscle activity achieves the optimal modulation in the expression of the psycho-physiological state of the subject.

In other embodiments, the present technology is directed to a method for optimally modulating the expression of a psycho physiological state in a subject, the method comprising the steps of: (a) eliciting and determining the individual pattern of facial expression markers (FEAMs) and corresponding muscle activity during the expression of a psycho physiological state in a subject (the Maximal Individual Prototypical Facial Expression of the psycho physiological state); (b) determining an optimal pattern of FEAMs and corresponding desired muscle activity of the subject for the psycho physiological state; (c) relating the optimal FEAM to a desired muscle activity that triggers the optimal FEAM; (d) identifying an agent and optimal dosage of the agent that modulates the FEAM and desired muscle activity; (e) identifying an optimal site on the body of the subject that modulates the desired FEAM and muscle activity when contacted with the agent; and (f) applying the optimal dosage of the agent to the body of the subject to implement the desired FEAMs and muscle activity, wherein the implementation of the FEAMs and desired muscle activity achieves the optimal modulation in the expression of the psycho physiological state of the subject.

Some aspects of embodiments may be implemented as a computer system. For example, various implementations may include digital and/or analog circuitry, computer hardware, firmware, software, or combinations thereof. Apparatus elements can be implemented in a computer program product tangibly embodied in an information carrier, e.g., in a machine-readable storage device, for execution by a programmable processor; and methods can be performed by a programmable processor executing a program of instructions to perform functions of various embodiments by operating on input data and generating an output. Some embodiments can be implemented advantageously in one or more computer programs that are executable on a programmable system including at least one programmable processor coupled to receive data and instructions from, and to transmit data and instructions to, a data storage system, at least one input device, and/or at least one output device. A computer program is a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example and not limitation, both general and special purpose microprocessors, which may include a single processor or one of multiple processors of any kind of computer. Generally, a processor will receive instructions and data from a read-only memory or a random access memory or both. The essential elements of a computer are a processor for executing instructions and one or more memories for storing instructions and data. Storage devices suitable for tangibly embodying computer program instructions and data include all forms of non-volatile memory, including, by way of example, semiconductor memory devices, such as EPROM, EEPROM, and flash memory devices; magnetic disks, such as internal hard disks and removable disks; magneto-optical disks; and, CD-ROM and DVD-ROM disks. The processor and the memory can be supplemented by, or incorporated in, ASICs (application-specific integrated circuits). In some embodiments, the processor and the member can be supplemented by, or incorporated in hardware programmable devices, such as FPGAs, for example.

In some implementations, each system may be programmed with the same or similar information and/or initialized with substantially identical information stored in volatile and/or non-volatile memory. For example, one data interface may be configured to perform auto configuration, auto download, and/or auto update functions when coupled to an appropriate host device, such as a desktop computer or a server.

In some implementations, one or more user-interface features may be custom configured to perform specific functions. An exemplary embodiment may be implemented in a computer system that includes a graphical user interface and/or an Internet browser. To provide for interaction with a user, some implementations may be implemented on a computer having a display device, such as an LCD (liquid crystal display) monitor for displaying information to the user, a keyboard, and a pointing device, such as a mouse or a trackball by which the user can provide input to the computer.

In various implementations, the system may communicate using suitable communication methods, equipment, and techniques. For example, the system may communicate with compatible devices (e.g., devices capable of transferring data to and/or from the system) using point-to-point communication in which a message is transported directly from the source to the receiver over a dedicated physical link (e.g., fiber optic link, point-to-point wiring, daisy-chain). The components of the system may exchange information by any form or medium of analog or digital data communication, including packet-based messages on a communication network. Examples of communication networks include, e.g., a LAN (local area network), a WAN (wide area network), MAN (metropolitan area network), wireless and/or optical networks, and the computers and networks forming the Internet. Other implementations may transport messages by broadcasting to all or substantially all devices that are coupled together by a communication network, for example, by using omni-directional radio frequency (RF) signals. Still other implementations may transport messages characterized by high directivity, such as RF signals transmitted using directional (i.e., narrow beam) antennas or infrared signals that may optionally be used with focusing optics. Still other implementations are possible using appropriate interfaces and protocols such as, by way of example and not intended to be limiting, USB 2.0, Firewire, ATA/IDE, RS-232, RS-422, RS-485, 802.11 a/b/g, Wi-Fi, Ethernet, IrDA, FDDI (fiber distributed data interface), token-ring networks, or multiplexing techniques based on frequency, time, or code division. Some implementations may optionally incorporate features such as error checking and correction (ECC) for data integrity, or security measures, such as encryption (e.g., WEP) and password protection.

A number of implementations have been described. Nevertheless, it will be understood that various modification may be made. For example, advantageous results may be achieved if the steps of the disclosed techniques were performed in a different sequence, or if components of the disclosed systems were combined in a different manner, or if the components were replaced or supplemented with other components. The functions and processes (including algorithms) may be performed in hardware, software, or a combination thereof, and some implementations may be performed on modules or hardware not identical to those described. Accordingly, other implementations are within the scope of the following claims.

The technology is directed to multidimensional methods to selectively analyze, target, modulate and/or optimize personal prototypical facial expression patterns and perceptual spaces that are characteristic of basic emotions and other psycho-physiological states.

What is claimed is:

1. A treatment system for modulating, approximating, or optimizing desired facial expressions by measuring personal degrees of expression of facial features in terms of Specific features, Relative distances, Elevations, Depression, Interacting features, and Coactivated distances (SREDIC) scores specifying expression intensity of individual Facial Expression Activated Markers (FEAMs) that are functionally classified and analyzed as personal relative distances between features, facial deformations and co-activated features before and after applying an agent or procedure to the face, head, or neck of a patient, the system comprising:
    a processor;
    a plurality of non-volatile program-memory locations coupled to the processor;
    a plurality of non-volatile data-memory locations coupled to the processor;
    a display device configured to be controlled by the processor; and,
    a camera configured to be controlled by the processor,
    wherein the plurality of non-volatile program-memory locations contains instructions that, when executed by the processor, cause the processor to perform operations comprising:
        receiving an image file of a full human face of a patient, the image file captured by the camera, the image file corresponding to a facial expression desired to be changed by the patient;
        sending for display on the display device the received image file;
        receiving, from the patient, information representative of a desired degree of change in the expression intensity of one or more selected Facial-Expression Activation Markers (FEAMs) of the facial expression desired to be changed;
        retrieving from the non-volatile data memory locations a SREDIC score that is associated with the selected one or more FEAMs, wherein the SREDIC score is based on personal relative distances between features, facial deformations and co-activated features of the patient associated with the selected one or more FEAMs, and corresponding facial muscles or facial muscle groups, wherein each of the corresponding facial muscles or facial muscle groups have an activation intensity level specified in terms of the degree and gradation level of FEAMs expressions;
        retrieving from the non-volatile data memory locations psycho-physiological states for which the SREDIC score is shared with, or functionally related to, the corresponding facial muscles or facial muscle groups of the retrieved SREDIC score;

receiving image files of facial expressions corresponding with the retrieved psycho-physiological states; and generating, in response to the SREDIC score, the retrieved expressions of psycho-physiological states, and the received desired degree of change in the expression intensity, a treatment program comprising one or more treatments at one or more treatment locations for approximating the desired facial expression while producing optimized corresponding changes in the expression of each of two or more psychophysiological states, each of the one or more treatment locations targeting one of the one or more selected FEAMs and corresponding facial muscles or facial muscle groups, each of the one or more treatment locations having an associated treatment and dosage information for each FEAM.

2. The treatment system of claim 1, further comprising a dosing station configured to be controlled by the processor according to the generated treatment program.

3. The treatment system of claim 1, wherein the instructions further comprise, sending for display on the display device an image file of a human face with treatment locations identified and annotated with treatment and dosage information.

4. The treatment system of claim 1, wherein the instructions further comprise sending for display on the display device, SREDIC score representative of an analysis of patterns of whole of the facial expressions obtained by measuring relevant personal activation intensity patterns of FEAMs and corresponding facial muscles that occur and co-occur during a period wherein maximal facial expression for relevant psycho-physiological states is being elicited from the patient.

5. The treatment system of claim 1, wherein the instructions further comprise sending control commands to the camera and receive image files from the camera.

6. The treatment system of claim 1, wherein the instructions further comprise mapping the image file of the human face onto a model of a human face by identifying the FEAMS from the image file of the human face and correlating the identified FEAMs to corresponding markers of the model of a human face.

7. A computer program product (CPP) tangibly embodied in a non-transitory computer readable storage device and containing instructions that, when executed, cause a processor to perform operations to determine an optimal treatment plan by measuring personal degrees of expression of facial features in terms of Specific features, Relative distances, Elevations, Depression, Interacting features, and Coactivated distances (SREDIC) scores specifying expression intensity of individual Facial Expression Activated Markers (FEAMs) that are functionally classified and analyzed as personal relative distances between features, facial deformations and co-activated features before and after for using agents or procedures capable of modifying FEAMs, the operations comprising:

receiving an image file of a human face, the image file corresponding to a facial expression desired to be changed by a user;

sending for display on a display device the received image file;

receiving, from the user, information representative of a desired degree of change in the expression intensity of one or more selected Facial-Expression Activation Markers (FEAMs) to obtain a more desirable facial expression;

retrieving a SREDIC score that is associated with the selected one or more FEAMs, wherein the SREDIC score is based on personal relative distances between features, facial deformations and co-activated features of the user associated with the selected FEAMs, and corresponding facial muscles or facial muscle groups, each of the corresponding facial muscles or facial muscle groups having an activation intensity level specified in terms of the degree and gradation level of FEAMs expressions;

retrieving psychophysiological states whose SREDIC scores are shared with, or functionally related to corresponding facial muscles or facial muscle groups of the selected SREDIC score;

receiving image files corresponding with the retrieved psycho-physiological states;

receiving, from the user, information representative of desired changes in the activation intensity of the FEAMs for two or more of the retrieved expressions of psychophysiological states; and, generating, in response to the SREDIC score, the retrieved expressions of psychophysiological states, and the received desired degree of change in the expression intensity, a treatment program comprising one or more treatment locations, each of the one or more treatment locations targeting one of the one or more treatments for optimally approximating the desired facial expression while producing optimized corresponding changes in the expression of each of two or more psycho-physiological states, each of the one or more treatment locations targeting one of the one or more selected FEAMs and corresponding facial muscles or facial muscle groups of a SREDIC score functionally associated with the one of the one or more selected FEAMs, each of the one or more treatment locations having an associated treatment and dosage information.

8. The computer program product of claim 7, further comprising instructions that, when executed, associates a weighting value with each of the retrieved psycho-physiological states associated with one of the one or more selected FEAMs and associated facial muscles or facial muscle groups.

9. The computer program product of claim 7, further comprising instructions that when executed, determine information representative of a desired amount of FEAM treatment includes a weighting value representative of the importance of treating the FEAM.

10. The computer program product of claim 7, further comprising instructions that, when executed, send control commands to the image capture device and receive image files from an image capture device.

11. The computer program product of claim 7, further comprising instructions that, when executed, map the image file of the human face onto a model of a human face.

12. The computer program product of claim 11, further comprising instructions that, when executed, identify facial markers from the image file of the human face and correlate the identified facial markers (FEAMs) to corresponding facial markers (FEAMs) of a model of a human face.

13. A computer program product (CPP) tangibly embodied in a non-transitory computer readable storage device and containing instructions that, when executed, cause a processor to perform operations to determine an optimal treatment plan by measuring personal degrees of expression of facial features in terms of Specific features, Relative distances, Elevations, Depression, Interacting features, and Coactivated distances (SREDIC) scores specifying expression intensity of individual Facial Expression Activated Markers (FEAMs) that are functionally classified and analyzed as personal relative distances between features, facial deformations and co-activated features before and after for using agents or procedures capable of modifying FEAMs, the operations comprising:

receiving an image file of a human face, the image file corresponding to a facial expression desired to be changed by a user;

sending for display on a display device the received image file;

receiving, from the user, information representative of a desired degree of change in expression intensity of one or more selected Facial-Expression Activation Markers (FEAMs) to obtain a more desirable facial expression;

retrieving a SREDIC score that is associated with the selected FEAM, wherein the SREDIC score is based on personal relative distances between features, facial deformations and co-activated features of the patient associated with the selected one or more FEAMs, and corresponding facial muscles or facial muscle groups, each of the corresponding facial muscles or facial muscle groups having an activation intensity level specified in terms of the degree and gradation levels of FEAMs expressions;

retrieving psycho-physiological states whose SREDIC scores are associated with one of the corresponding facial muscles or facial muscle groups of the retrieved SREDIC score;

receiving image files corresponding with the retrieved psycho-physiological states; and, means for auto-generating a treatment plan based upon the SREDIC score, the retrieved expressions of psycho-physiological states, and the received desired degree of change in the expression intensity, the treatment plan comprising one or more FEAM treatment locations, each of the one or more treatment locations targeting one of the one or more selected one or more FEAMs and corresponding facial muscles or facial muscle groups, each of the one or more treatment locations having an associated treatment and dosage information.

14. The computer program product of claim 13, wherein the means for auto-generating a treatment plan comprises means for weighting the retrieved psycho-physiological states whose SREDIC score are shared with, or functionally related to, retrieved SREDIC scores of the one or more selected FEAMS and the corresponding facial muscles or facial muscle groups.

15. The computer program product of claim 13, further comprising instructions that, when executed, resolves a conflict between information representative of a desired amount of FEAM treatment and other associated conflicting SREDIC scores representative of a desired amount of FEAM treatment.

16. The computer program product of claim 15, wherein resolving the conflict includes sending, for display on the display device, the information representative of a desired amount of FEAM treatment with the other associated conflicting SREDIC scores representative of a desired amount of FEAM treatment, for review by a physician.

17. The computer program product of claim 15, wherein resolving the conflict includes using weighting values associated with each of a plurality of conflicting FEAM treatments associated with the other associated conflicting SREDIC scores derived from multiple expressions of different psycho-physiological states.

\* \* \* \* \*